(12) United States Patent
Miyazaki et al.

(10) Patent No.: US 7,762,788 B2
(45) Date of Patent: Jul. 27, 2010

(54) FLUID CONVEYANCE SYSTEM AND FLUID CONVEYANCE DEVICE

(75) Inventors: Hajime Miyazaki, Matsumoto (JP); Kazuo Kawasumi, Suwa (JP)

(73) Assignee: Seiko Epson Corporation (JP)

( * ) Notice: Subject to any disclaimer, the term of this patent is extended or adjusted under 35 U.S.C. 154(b) by 157 days.

(21) Appl. No.: 11/831,185

(22) Filed: Jul. 31, 2007

(65) Prior Publication Data

US 2008/0031740 A1 Feb. 7, 2008

(30) Foreign Application Priority Data

Aug. 1, 2006 (JP) ............................. 2006-209518
Jun. 25, 2007 (JP) ............................. 2007-165919

(51) Int. Cl.
*F04B 49/00* (2006.01)

(52) U.S. Cl. ....................... 417/212; 417/213; 417/279; 417/280

(58) Field of Classification Search ................... 417/12, 417/44.1, 212–213, 280, 290, 474, 477.1–477.14
See application file for complete search history.

(56) References Cited

U.S. PATENT DOCUMENTS

| | | | | |
|---|---|---|---|---|
| 3,737,251 A | | 6/1973 | Berman et al. | |
| 4,913,624 A | * | 4/1990 | Seki et al. | 417/2 |
| 5,018,945 A | * | 5/1991 | D'Silva | 417/12 |
| 5,074,756 A | * | 12/1991 | Davis | 417/45 |
| 5,239,319 A | * | 8/1993 | Miyazaki et al. | 340/679 |
| 5,395,320 A | * | 3/1995 | Padda et al. | 604/65 |
| 6,393,338 B1 | * | 5/2002 | Kemnitz | 700/231 |
| 6,671,611 B1 | * | 12/2003 | Peltier | 701/104 |
| 6,829,542 B1 | * | 12/2004 | Reynolds et al. | 702/34 |
| 6,986,646 B2 | * | 1/2006 | Bettenhausen et al. | 417/53 |
| 2002/0183693 A1 | * | 12/2002 | Peterson et al. | 604/151 |
| 2006/0002799 A1 | * | 1/2006 | Schann et al. | 417/1 |
| 2006/0271020 A1 | * | 11/2006 | Huang et al. | 604/890.1 |
| 2007/0258827 A1 | * | 11/2007 | Gierke | 417/6 |

FOREIGN PATENT DOCUMENTS

JP 3177742 4/2001

* cited by examiner

*Primary Examiner*—Devon C Kramer
*Assistant Examiner*—Christopher Bobish
(74) *Attorney, Agent, or Firm*—Harness, Dickey & Pierce, P.L.C.

(57) ABSTRACT

A fluid conveyance system includes: a fluid conveyance device including a micro pump module which compresses a flexible tube communicating with a fluid containing receptacle and discharges a fluid, a memory device furnished on the micro pump module which stores individual identification data of the micro pump module, and a power source; a discharge data processing device which stores basic data for driving the fluid conveyance device; and a communication device having a communication unit which interconnects the fluid conveyance device and the discharge data processing device, wherein the discharge data processing device inputs discharge data, for discharging a desired discharge amount of a fluid, calculated from the identification data and the basic data read via the communication device, into the memory device via the communication device, and the fluid conveyance device is driven based on the discharge data.

7 Claims, 43 Drawing Sheets

FIG. 8

| BASIC DATA SETTING | | | |
|---|---|---|---|
| STEPPING MOTOR DRIVE PULSE FREQUENCY (Hz): | 45 | BATTERY CAPACITY (mAH): | 39.0 |
| MICRO PUMP DISCHARGE AMOUNT BASIC VALUE (μl/REVOLUTION): | 4.000 | SAFETY RATE: | 0.90 |
| CORRECTION COEFFICIENT: | 1000 | CPU EXECUTION TIME CONSUMPTION CURRENT (μA): | 1.7 |
| MICRO PUMP DISCHARGE AMOUNT (μl/REVOLUTION): | 4.000 | CPU HALT TIME CONSUMPTION CURRENT (μA): | 0.1 |
| MAXIMUM DISCHARGE SPEED UPPER LIMIT VALUE (μl/H): | 15 | POWER SOURCE VOLTAGE DETECTION CIRCUIT (SVD): | OFF ● ON |
| MINIMUM SET DISCHARGE SPEED (μl/H): | NO LOWER LIMIT | POWER SOURCE VOLTAGE DETECTION CIRCUIT (SVD) DETECTION INTERVAL (min.): | 30 |
| MAXIMUM DISCHARGE TIME UPPER LIMIT VALUE (H): | NO UPPER LIMIT | POWER SOURCE VOLTAGE DETECTION CIRCUIT (SVD) DETECTION VOLTAGE (V): | 1.22 |
| INITIAL DRIVE SPEED (μl/H): | 15 | RESERVOIR CAPACITY (μl): | 500 |
| INITIAL DRIVE TIME (s): | 30 | RESERVOIR LOWER LIMIT CAPACITY (μl): | 0 |
| STEPPING MOTOR PULSE WIDTH (ms): | 5.86 | OPERATION MODE: | NORMAL ● TEST |
| STEPPING MOTOR DECELERATION RATIO: | 21600 | CORRECTION OF SET DISCHARGE SPEED (EVAPORATION) (μl): | 0.00 |
| STEPPING MOTOR CONSUMPTION CURRENT (μA/Step): | 3.0 | CORRECTION OF INFUSION AMOUNT (EVAPORATION) (μl): | 0.0 |

REGISTER    CANCEL

| DISCHARGE DATA SETTING: SINGLE (TEST1) | |
|---|---|
| MAXIMUM SETTABLE DISCHARGE SPEED ($\mu l/H$): | 15.0 |
| DISCHARGE SPEED SETTING ($\mu l/H$): | 0.0 |
| MAXIMUM SETTABLE DISCHARGE TIME (H): | 0.0 |
| MAXIMUM DISCHARGE AMOUNT ($\mu l$): | 0.0 |
| DISCHARGE TIME SETTING (H): | 0.0 |
| SET DISCHARGE AMOUNT ($\mu l$): | 0.00 |
| REGISTER | CANCEL |

FIG.14

| DISCHARGE DATA SETTING: SINGLE (TEST1) | |
|---|---|
| MAXIMUM SETTABLE DISCHARGE SPEED ($\mu l/H$): | 15.0 |
| DISCHARGE SPEED SETTING ($\mu l/H$): | 10.0 |
| MAXIMUM SETTABLE DISCHARGE TIME (H): | 339.0 |
| MAXIMUM DISCHARGE AMOUNT ($\mu l$): | 3390.0 |
| DISCHARGE TIME SETTING (H): | 50.0 |
| SET DISCHARGE AMOUNT ($\mu l$): | 500.00 |
| REGISTER | CANCEL |

| DISCHARGE DATA SETTING: MULTI NO.1 (TEST1) | |
|---|---|
| MAXIMUM SETTABLE DISCHARGE SPEED (μl/H): | 15 |
| DISCHARGE SPEED SETTING (μl/H): | 0.0 |
| MAXIMUM SETTABLE DISCHARGE TIME (H): | 0 |
| MAXIMUM DISCHARGE AMOUNT (μl): | 0.0 |
| DISCHARGE TIME SETTING (H): | 0.0 |
| NO. 1 SET DISCHARGE AMOUNT (μl): | 0.00 |
| TOTAL SET DISCHARGE AMOUNT (μl): | 0.00 |

[ REGISTER ]   [ DELETE ]   [ CANCEL ]

FIG.19

| DISCHARGE DATA SETTING: MULTI NO.1 (TEST1) | |
|---|---|
| MAXIMUM SETTABLE DISCHARGE SPEED (μl/H): | 15.0 |
| DISCHARGE SPEED SETTING (μl/H): | 10.0 |
| MAXIMUM SETTABLE DISCHARGE TIME (H): | 339.0 |
| MAXIMUM DISCHARGE AMOUNT (μl): | 3390.0 |
| DISCHARGE TIME SETTING (H): | 10.0 |
| NO. 1 SET DISCHARGE AMOUNT (μl): | 100.00 |
| TOTAL SET DISCHARGE AMOUNT (μl): | 100.00 |

[ REGISTER ]   [ DELETE ]   [ CANCEL ]

DISCHARGE DATA SETTING: MULTI (TEST1)

- No. 1 — ○ INVALID  ● VALID
- No. 2 — ● INVALID  ○ VALID
- No. 3 — ● INVALID  ○ VALID
- No. 4 — ● INVALID  ○ VALID
- No. 5 — ● INVALID  ○ VALID

TOTAL SET DISCHARGE TIME (H): 10.0
TOTAL SET DISCHARGE AMOUNT ($\mu l$): 100.00

RETURN

FIG.20

DISCHARGE DATA SETTING: MULTI (TEST1)

- No. 1 — ○ INVALID  ● VALID
- No. 2 — ○ INVALID  ● VALID
- No. 3 — ○ INVALID  ● VALID
- No. 4 — ○ INVALID  ● VALID
- No. 5 — ○ INVALID  ● VALID

TOTAL SET DISCHARGE TIME (H): 65.0
TOTAL SET DISCHARGE AMOUNT ($\mu l$): 575.00

RETURN

| MICRO PUMP SYSTEM | | | | |
|---|---|---|---|---|
| PUMP NAME | OPERATION STATUS | ADDITIONAL INFUSION TIME | DISCHARGE FINISHING TIME | |
| TEST 1 | OPERATION IN PROGRESS | 2006/ 2/20 11:39 | 2006/ 2/20 11:41 | |

NEW
UPDATE/CONFIRM
PRINT
DELETE
SYSTEM SETTINGS
FINISH

| MICRO PUMP DISCHARGE INFORMATION (MODULE: TEST2) | |
|---|---|
| MICRO PUMP OPERATION DATA: | SINGLE DATA |
| MICRO PUMP STOPPING REASON: | VOLTAGE REDUCTION |
| MICRO PUMP DRIVE TIME (H): | 0.0 |
| TOTAL MICRO PUMP DISCHARGE AMOUNT ($\mu$l): | 0.00 |

DISCHARGE DATA SETTING SELECTION: MULTI (TEST1)

| No. 1 | ◯ INVALID | ◉ VALID |
|---|---|---|
| No. 2 | ◯ INVALID | ◉ VALID |
| No. 3 | ◯ INVALID | ◉ VALID |
| No. 4 | ◯ INVALID | ◉ VALID |
| No. 5 | ◯ INVALID | ◉ VALID |

TOTAL SET DISCHARGE TIME (H): 530.0
TOTAL SET DISCHARGE AMOUNT ($\mu$l): 4950.00

RETURN

FIG.57

DISCHARGE DATA SETTING: MULTI No.5 (TEST1)

| | |
|---|---|
| MAXIMUM SETTABLE DISCHARGE SPEED (µl/H): | 15 |
| DISCHARGE SPEED SETTING (µl/H): | 10.0 |
| MAXIMUM SETTABLE DISCHARGE TIME (H): | 110 |
| MAXIMUM DISCHARGE AMOUNT (µl): | 1100.0 |
| DISCHARGE TIME SETTING (H): | 100.0 |
| No. 5 SET DISCHARGE AMOUNT (µl): | 1000.00 |
| TOTAL SET DISCHARGE AMOUNT (µl): | 4550.00 |

[ REGISTER ]  [ DELETE ]  [ CANCEL ]

FIG.58

DISCHARGE DATA SETTING SELECTION: MULTI (TEST1)

| No. 1 | ○ INVALID | ● VALID |
| No. 2 | ○ INVALID | ● VALID |
| No. 3 | ○ INVALID | ● VALID |
| No. 4 | ○ INVALID | ● VALID |
| No. 5 | ● INVALID | ○ VALID |

TOTAL SET DISCHARGE TIME (H): 270.0
TOTAL SET DISCHARGE AMOUNT (µl): 2700.00

[ RETURN ]

FIG.59

| DISCHARGE DATA SETTING: MULTI No 4 (TEST 1) | |
|---|---|
| MAXIMUM SETTABLE DISCHARGE SPEED ($\mu$l/H): | 15 |
| DISCHARGE SPEED SETTING ($\mu$l/H): | 10.0 |
| MAXIMUM SETTABLE DISCHARGE TIME (H): | 190 |
| MAXIMUM DISCHARGE AMOUNT ($\mu$l): | 1900.0 |
| DISCHARGE TIME SETTING (H): | 150 |
| No. 4 SET DISCHARGE AMOUNT ($\mu$l): | 1000.00 |
| TOTAL SET DISCHARGE AMOUNT ($\mu$l): | 3750.00 |

REGISTER   DELETE   CANCEL

FIG.60

DISCHARGE DATA SETTING SELECTION: MULTI (TEST 1)

| No. 1 | ○ INVALID | ● VALID |
|---|---|---|
| No. 2 | ○ INVALID | ● VALID |
| No. 3 | ○ INVALID | ● VALID |
| No. 4 | ○ INVALID | ● VALID |
| No. 5 | ○ INVALID | ● VALID |

TOTAL SET DISCHARGE TIME (H):  530.0
TOTAL SET DISCHARGE AMOUNT ($\mu$l):  4950.00

RETURN

FIG.61

FLUID CONVEYANCE SYSTEM AND FLUID CONVEYANCE DEVICE

BACKGROUND

1. Technical Field

The present invention relates to a fluid conveyance system which, including a miniature fluid conveyance device, a discharge data processing device, and a communication device, individually recognizes and drives the fluid conveyance device, and to the fluid conveyance device.

2. Related Art

In recent years, a use in medical treatment of a miniature pump for continuously administering a minute amount of chemical liquid, in a form of a gentle stream, to a patient is being researched.

For example, as a miniature peristaltic pump device suitable for mounting in a human body for injecting an aqueous chemical liquid or the like at a low speed and continuously, there is a miniature peristaltic pump device which, a pump rotor being attached to a shaft, a plurality of rollers being disposed on the rotor, in an evenly dispersed condition on a periphery of the shaft, the rollers carrying out a rotating motion while rolling along a flexible tube, and the tube being pressed against a backing which surrounds the tube over a range of a circular arc of a prescribed length, carries out a suction and release of a fluid such as a chemical liquid.

As this kind of miniature peristaltic pump device, a kind of miniature peristaltic pump device has been known in which, including a stepping motor as a power source, the stepping motor drives at a rotation speed set in advance by a block IC including a control circuit, and a desired discharge amount is obtained (for example, refer to Japanese Patent 3177742).

Also, as the miniature peristaltic pump device, a miniature peristaltic pump device has been known which includes, on a housing, a miniature peristaltic pump, input switches for setting a fluid discharge amount of the miniature peristaltic pump in a plurality of stages, and selecting and setting a discharge amount of the fluid from among the plurality of set stages, and a display (for example, refer to U.S. Pat. No. 3,737,251).

In this kind of Japanese Patent 3177742, although it is possible to set or change a discharge amount of a chemical fluid or the like, depending on a number of frequency divider stages which receive a signal supplied from a time base, a deceleration ratio of a gear mechanism, and a kind of motor used, it is necessary to manufacture having decided in advance setting conditions thereof. However, discharge conditions once set being fixed, there is a problem in that it is difficult to change a type of usage and conditions of a chemical fluid administration at will, and set a fluid discharge amount.

Also, according to U.S. Pat. No. 3,737,251, it is possible, by providing switches for adjusting a discharge amount of a fluid, a display and a peristaltic pump, on a housing, to adjust the discharge amount but, as the miniature peristaltic pump, switches and display are placed on the housing, miniaturization is difficult with this kind of configuration, and it is not possible to mount it inside a body of a small animal with an object of a new chemical development or the like.

Also, in both the previously described Japanese Patent 3177742 and U.S. Pat. No. 3,737,251, a plurality of fluid conveyance devices existing, when selectively using a fluid conveyance device with pre-set discharge conditions, it is not possible to individually recognize the fluid conveyance device. Consequently, it being conceivable that a human error occurs whereby a fluid conveyance system user (referring to a user) uses a fluid conveyance device in which wrong discharge conditions have been set, there is a kind of problem in that there will be serious consequences when using in medical treatment or the like.

Also, when using a battery or the like as a power source, although, when stopping the fluid conveyance device during use, then reusing it, it is necessary to drive with a discharge condition program corresponding to a remaining capacity of the battery, in the previously described Japanese Patent 3177742 and U.S. Pat. No. 3,737,251, there not being that kind of function, it is not possible to repeatedly reuse the fluid conveyance device until the battery capacity expires.

Furthermore, in the event that a remaining amount of a battery capacity of each of a plurality of fluid discharge devices differs, as it is not possible to recognize a battery remaining capacity for one fluid discharge device, it being unclear how much longer it is possible to drive the relevant fluid discharge device, there is a problem in that it is not possible to efficiently use the fluid conveyance device, such as by re-driving.

SUMMARY

The invention, being contrived with an object of solving at least some of the heretofore described problems, can be realized as the following aspects.

A fluid conveyance system according to an aspect of the invention includes a fluid conveyance device, a discharge data processing device and a communication device. The fluid conveyance device includes a micro pump module which compresses a flexible tube communicating with a fluid containing receptacle and discharges a fluid, a memory device furnished on the micro pump module and which stores individual identification data of the micro pump module, and a power source. The discharge data processing device stores basic data for driving the fluid conveyance device. The communication device has a communication unit which interconnects the fluid conveyance device and the discharge data processing device.

The discharge data processing device inputs discharge data, for discharging a desired discharge amount of a fluid, calculated from the identification data and the basic data read via the communication device, into the memory device via the communication device, and the fluid conveyance device is driven based on the discharge data.

According to the fluid conveyance system, individual identification data being input into the memory device of the micro pump module, as it is possible for the discharge data processing device, via the communication device, to read and recognize the identification data of the micro pump module, it not being necessary for a fluid conveyance system user (who may be referred to hereafter as a user) to artificially identify the micro pump module, it is possible to prevent a kind of mistake such as inputting erroneous discharge data into the micro pump module to be used, and driving it. This has a benefit of being able to prevent an effect which cannot be ignored when using the fluid conveyance system in medical treatment, a living organism experiment, or the like.

Also, as the discharge data processing device, via the communication device, reads the individual identification data of the micro pump module, it is possible to recognize the micro pump module, via the communication device, after use too.

Also, it is preferable that the identification data include at least an identification code of the micro pump module, a manufacturing period, and a correction coefficient for correcting a discharge amount fluctuation due to a fluctuation in inner diameter of the tube.

The correction coefficient for correcting the discharge fluctuation due to the fluctuation in the inner diameter of the tube is expressed as a ratio between a design tube inner diameter (the inner diameter can be converted into a sectional area over which a fluid flows) and an inner diameter of a tube used in a fluid conveyance device to be driven, or as a ratio between a discharge amount of a fluid conveyance device which includes a tube to be taken as a standard, and a discharge amount of the fluid conveyance device to be driven. Consequently, as the fluid conveyance device is driven by discharge data in which the fluctuation in the inner diameter of the individual tube to be driven has been corrected, it is possible to eliminate an effect of the fluctuation in the inner diameter of the tube on the discharge amount of the fluid.

Also, by a fluid conveyance system provider (who may be referred to hereafter as a manufacturer) inputting the identification data into the micro pump module at the time of manufacture, it is possible to recognize, and start using, each micro pump module.

Furthermore, by mounting the fluid conveyance device to be driven on the discharge data processing device and the communication device, the discharge data processing device being able to recognize the identification data, it is unnecessary for the user to input the identification data into the discharge data processing device, so there is also a benefit of being able to eliminate a bother of inputting, and prevent an input error.

Also, it is preferable that the power source is a battery, the basic data further include an initial battery capacity of the power source, and the discharge data include a discharge speed and a discharge time of the fluid, and that the discharge data processing device, including a calculation device which calculates a remaining capacity of the battery from a consumption current value and a discharge time of the micro pump module, transmits a discharge speed and a discharge time of a re-drivable range, based on the remaining capacity, to the memory device, and the fluid conveyance device is re-driven based on the discharge speed and the discharge time.

Herein, for example, a primary battery and a rechargeable secondary battery are included as the battery.

By so doing, as it is possible for the user to know the remaining capacity of the battery after the drive of the fluid conveyance device has finished, it is possible to repeatedly reuse the fluid conveyance device until the battery capacity expires.

Furthermore, as it is possible to set the discharge speed and discharge time in accordance with the remaining capacity of the battery, it is possible to prevent the battery capacity expiring and the fluid conveyance device stopping while being used, and to increase safety.

Also, it is preferable that the identification data include at least an identification code, a manufacturing period, and the correction coefficient, and that the identification data are input from the discharge data processing device, via the communication device, into the micro pump module.

By so doing, in the event that the identification data input in advance into the micro pump module at a time of manufacturing should be deleted, it is possible to input the identification data from the discharge data processing device.

Also, it is preferable that the identification data include at least an identification code, a manufacturing period, and the correction coefficient, and a display portion which displays the identification data is disposed in a position opposite a reader furnished on the communication device of the micro pump module, and that the identification data is input by the reader, via the communication device, from the display portion into the discharge data processing device, and discharge data calculated based on the basic data and the identification data are transmitted to the micro pump module via the communication device.

Herein, for example, a barcode, a QR code or the like, is represented as the display portion which displays the identification data.

In a case of assuming that the previously described memory device storing the identification data is an RAM (Random Access memory) or the like, it is conceivable that the identification data could be deleted by an effect of static electricity or the like. However, by displaying the identification data on the display portion by the barcode or the QR code, and recognizing them with the reader, it is possible to prevent the identification data from being deleted by the effect of the static electricity or the like.

Also, a fluid conveyance device includes a micro pump module which compresses a flexible tube communicating with a fluid containing receptacle and discharges a fluid, a memory device furnished on the micro pump module and which stores individual identification data of the micro pump module, and a power source. A discharge data processing device, which stores basic data for driving the fluid conveyance device, inputs discharge data for discharging a desired discharge amount of a fluid, calculated from the identification data and the basic data read via a communication device, which has a communication unit which interconnects the fluid conveyance device and the discharge data processing device, into the memory device via the communication device, and the fluid conveyance device is driven based on the discharge data.

The individual identification data being input into the memory device of the micro pump module, as it is possible for the discharge data processing device, via the communication device, to read and recognize the identification data of the micro pump module, it not being necessary for the user to artificially identify the micro pump module, it is possible to prevent a kind of mistake such as inputting erroneous discharge data into the micro pump module to be used, and driving it.

Also, as the discharge data processing device, via the communication device, reads the individual identification data of the micro pump module, it is possible to recognize the fluid conveyance device, via the communication device, after use too.

BRIEF DESCRIPTION OF THE DRAWINGS

The invention will be described with reference to the accompanying drawings, wherein like numbers reference like elements.

FIG. 8 is an illustration showing an operation for setting the basic data.

FIG. 14 is an illustration showing a setting operation of a discharge speed and a discharge time.

FIG. 15 is an illustration showing a condition in which the discharge capacity and the discharge time have been set.

FIG. 17 is an illustration showing a "Discharge data setting selection" screen on which the multi-drive has been selected.

FIG. 18 is an illustration showing an operation setting the discharge capacity and the discharge time at a time of the multi-drive.

FIG. 19 is an illustration showing a condition in which the discharge capacity and the discharge time have been set at the time of the multi-drive.

FIG. 20 is an illustration showing a setting condition of each micro pump during the multi-drive.

FIG. 21 is an illustration showing that the discharge data have been set in all of the micro pumps during the multi-drive.

FIG. 34 is an illustration showing a condition in which the fluid conveyance device is actually being driven.

FIG. 56 is an illustration showing the acquired discharge information data.

FIG. 57 is an illustration showing a screen carrying out a discharge data correction after a discharge data registration during the multi-drive.

FIG. 58 is an illustration showing a correction screen of discharge data being input.

FIG. 59 is an illustration showing one process of a correction of the discharge data being input.

FIG. 60 is an illustration showing a condition in which the discharge data being input has been corrected.

FIG. 61 is an illustration showing a condition in which the correction of the discharge data being input is complete.

DESCRIPTION OF EXEMPLARY EMBODIMENTS

Hereafter, a description will be given of embodiments of the invention, based on the drawings.

Figure 1:
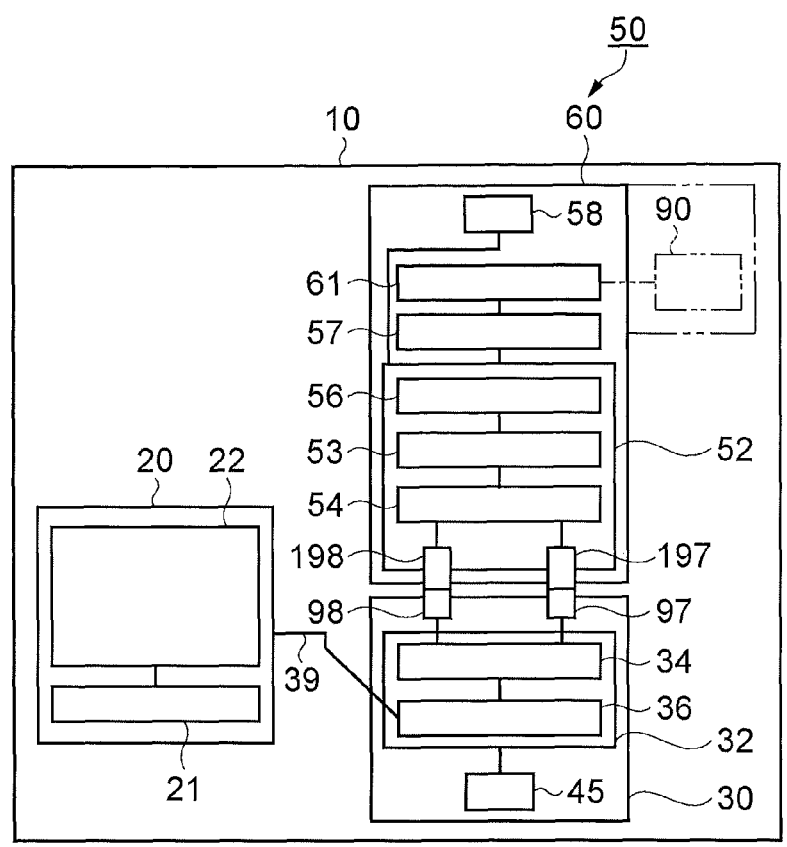
FIG. 1 is a block diagram showing a configuration of a fluid conveyance system according to an embodiment 1.
Figure 2:
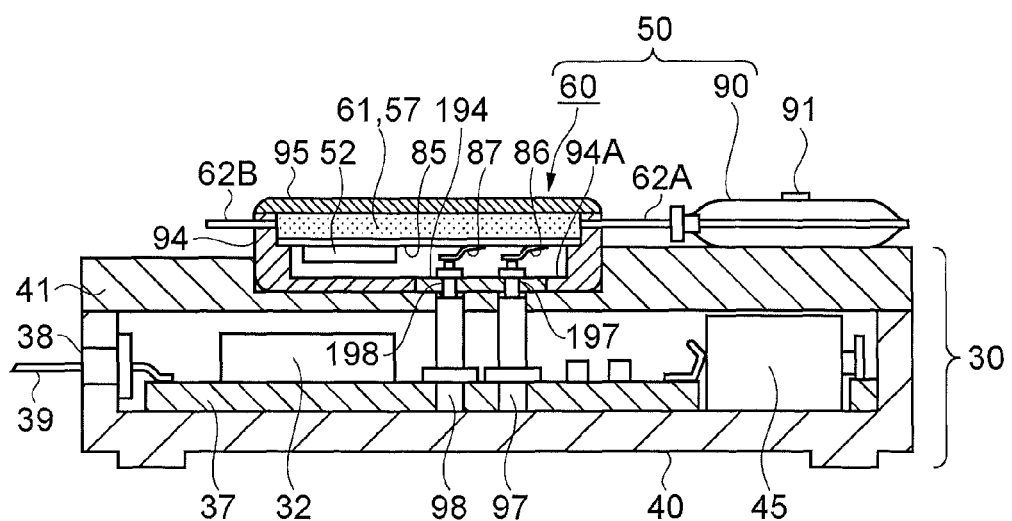
FIG. 2 is a sectional view showing an outline structure of a communication device and a fluid conveyance device, according to the embodiment 1, in a mounted condition.
Figure 3:
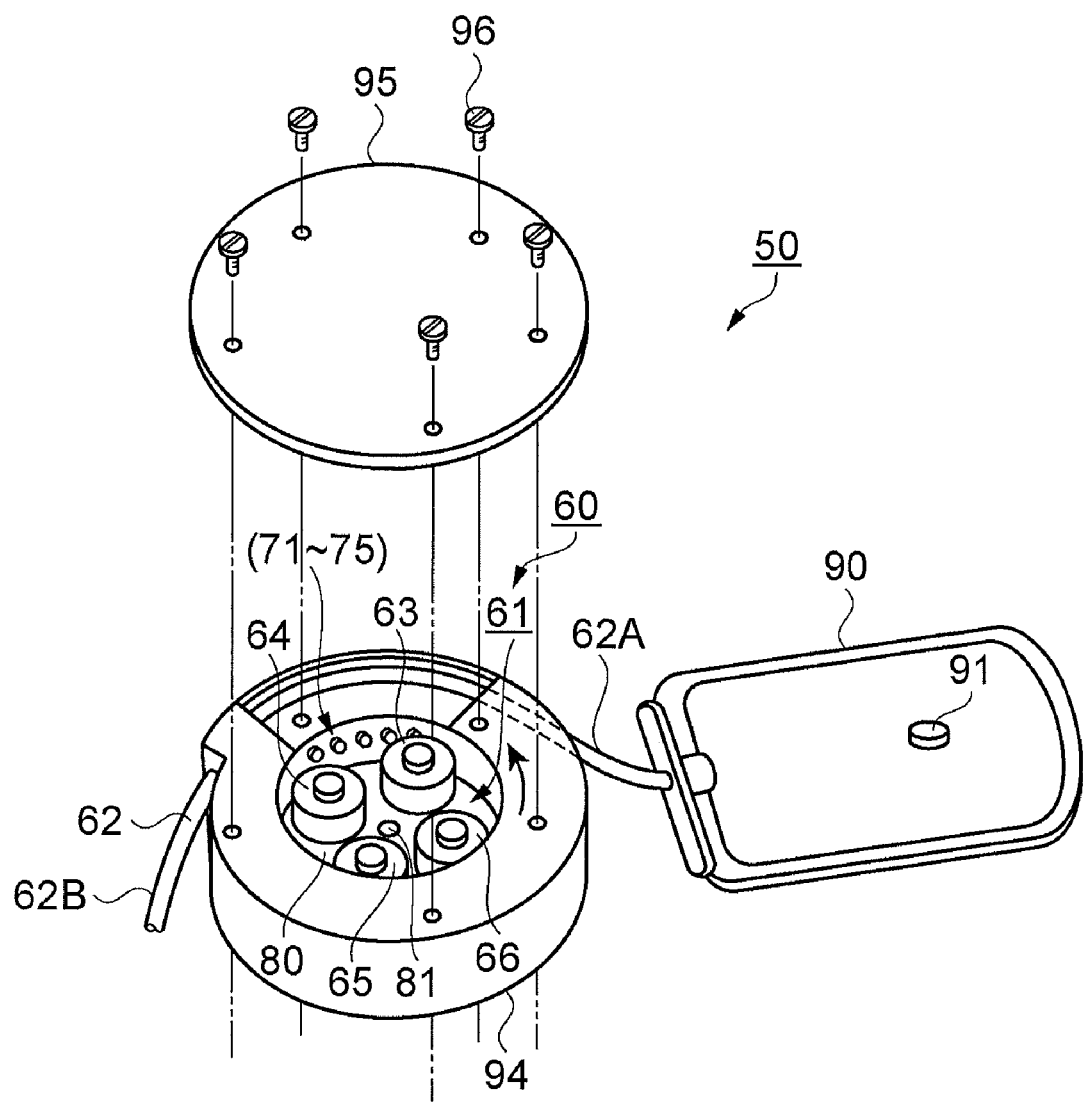
FIG. 3 is an exploded perspective view showing a structure of the fluid conveyance device according to the embodiment 1.

FIG. 1 to FIG. 3 show a configuration of a fluid conveyance system according to an embodiment 1 of the invention, while FIG. 4A to FIG. 6 show an input of data on, and an operation of, the fluid conveyance system.

Embodiment 1

In Embodiment 1, a description will be given exemplifying with a fluid conveyance system which employs a micro pump module (which may be referred to hereafter as a micro pump), mountable inside a living organism, which realizes a discharge of a fluid (which may be referred to as a chemical liquid) in microliter (µl) units.

FIG. 1 is a block illustration showing one example of the configuration of the fluid conveyance system according to Embodiment 1. In FIG. 1, the fluid conveyance system 10 is configured of, as its basic components, a discharge data processing device 20 (which may be referred to hereafter as a PC (Personal Computer) 20), a communication device 30, and a fluid conveyance device 50.

An operating portion 21, as an input device which inputs drive conditions of the fluid conveyance device 50, a display 22, which displays the input drive conditions and a drive result, as well as a calculation processing function, a memory function, and a writing and reading device of a storage medium such as a CD-ROM (Read Only Memory), which a general PC has, are stored in the PC 20. The operating portion 21 is a keyboard. The drive conditions input into the PC 20 are transmitted to the communication device 30 via a USB (Universal Serial Bus) cable 39.

Although a detailed description will be given hereafter, a manufacturer and a user each possess and operate the PC 20.

As the communication device, it is possible to select a wireless communication unit, an infrared ray communication unit, a wired communication unit, or the like as a way of communicating with the fluid conveyance device 50, but in the embodiment, a description will be given exemplifying with a communication device using a wired type of communication unit as a representative example.

The communication device 30 is configured of a communication control circuit 32, having a memory circuit 36 and a transceiving control circuit 34, and a battery 45 as a power source. Also, connection terminals 97 and 98 are connected to the transceiving control circuit 34.

Communication is achieved by causing these connection terminals 97 and 98 to come into contact with connection terminals 197 and 198 furnished on the fluid conveyance device 50.

The data input from the PC 20 are stored in the memory circuit 36, converted into a transmission signal by the transceiving control circuit 34, and input into a transceiving control circuit 54 of the fluid conveyance device 50 via the connection terminals 97 and 98.

Although, as the power source, a structure is shown in which the battery 45 is built into the communication device 30, a structure which takes in commercial energy from an exterior is also acceptable. In this case, a power source control circuit is installed. When employing the battery 45, a not-shown battery voltage detection circuit is included.

Also, it is also possible to introduce energy from the USB cable 39 which connects the PC 20 and the communication device 30.

The fluid conveyance device 50 is configured of the micro pump module 60 and, as a fluid containing receptacle which contains a fluid, a reservoir 90. The micro pump module 60 is configured of a pump unit 61, which conveys a fluid by compressing a flexible tube 62 (refer to FIG. 3), a pump drive unit 57, which drives the pump unit 61, a drive control circuit 56, which controls an overall drive of the pump drive unit 57, a memory circuit 53, as a memory device which stores basic data, discharge data, and identification data input from the discharge data processing device 20, and the transceiving control circuit 54, for controlling a transmission to and reception from the communication device 30. An RAM is employed as the memory circuit 53.

Also, the heretofore described connection terminals 197 and 198 being connected to the transceiving control circuit 54, the drive control circuit 56 and the transceiving control circuit 54, as a fluid conveyance device control circuit 52, are configured in the embodiment as a one chip IC. The micro pump module 60 incorporating a battery 58 as a power source, although a button type or coin type of miniature primary battery is being employed, it is also possible to employ a rechargeable secondary battery.

Although not shown, a battery voltage detection circuit for detecting a voltage of the battery 58, a timer which measures a drive time, a memory, as a drive pulse setting device which pre-sets a plurality of drive pulse conditions of a stepping motor, to be described hereafter, and a stepping motor drive control circuit are included in the drive control circuit 56.

The manufacturer inputs the basic data into discharge data processing device software, writes it onto the CD-ROM or the like, and hands it over to the user. At a time of manufacture, individual identification data of the micro pump module 60 are input into the memory circuit 53, represented by the RAM of the micro pump module 60. An identification code, a manufacturing period (a manufacturing time and date), and a correction coefficient for correcting a discharge amount fluctuation due to fluctuation in inner diameter of the tube 62 are included as the identification data. The basic data are input by the user inserting the CD-ROM into the PC 20 which the user possesses, and installing the discharge data processing device software. Then, the discharge data processing device 20 inputs the discharge data set by the manufacturer or the user, and transmits the data to the fluid conveyance device 50 via the communication device 30, and the fluid conveyance device 50 is driven based on the data.

Also, as the storage medium, not being limited to the CD-ROM, it is also acceptable to use a memory card or another storage medium.

Continuing, a description will be given, with reference to the drawings, of an aspect in which the communication device 30 and the fluid conveyance device 50 according to the embodiment are connected. FIG. 1 will also be referred to.

FIG. 2 is a sectional view showing an outline structure of a condition in which the communication device 30 and the fluid conveyance device 50 are mounted, and intercommunication is possible. In FIG. 2, the fluid conveyance device 50 is mounted on a top surface of the communication device 30.

The micro pump module 60 is mounted inside a depression formed in a cover 41 of the communication device 30. At this time, a dimension setting is done which enables an accurate positioning of each of the micro pump module 60 and the depression.

The communication device 30 is configured by a circuit substrate 37, a communication control circuit 32 mounted on a surface of the circuit substrate 37, other circuit elements, the battery 45 as the power source, and a USB connector 38 being mounted inside a housing configured of a casing 40 and the cover 41. The depression being formed in the top surface of the cover 41, the micro pump module 60 is mounted inside the depression. The USB connector 38 is connected to the PC 20 by the USB cable 39. In the event that the energy is supplied by the USB connector 38, the battery 45 is not necessary.

The two connection terminals 97 and 98 being implanted upright in the circuit substrate 37, the distal portions of the connection terminals 97 and 98 penetrate the cover 41, and protrude on the micro pump module 60 side. The connection terminals 97 and 98 are each connected to a terminal (not shown) of the transceiving control circuit 34 built into the communication control circuit 32, by a wiring pattern formed on the circuit substrate 37.

The micro pump module 60 has a circuit substrate 85, a fluid conveyance device control circuit 52 mounted on a surface of the circuit substrate 85, the pump unit 61 and the pump drive unit 57, and the not-shown battery 58, stored in a housing formed of a casing 94 and a cover 95. Connection terminal springs 86 and 87 being furnished on the circuit substrate 85, the connection terminal springs 86 and 87 are each connected to the transceiving control circuit 54 (not shown) built into the fluid conveyance device control circuit 52, by a wiring pattern formed on the circuit substrate 85.

A sealing member 194 being mounted in a bottom 94A of the casing 94 of the micro pump module 60, the connection terminals 197 and 198, which penetrate the sealing member 194, are implanted upright. The connection terminals 197 and 198 are provided, respectively, in positions opposite the connection terminals 97 and 98 provided in the communication device 30.

The sealing member 194 and casing 94, and the sealing member 194 and connection terminals 197 and 198, being respectively adhesive attached, a configuration is such that waterproofing is maintained, and the fluid does not enter an interior.

When the micro pump module 60 is mounted on the communication device 30, the connection terminals 97 and 98 provided on the communication device 30 are connected respectively to the connection terminals 197 and 198 provided on the micro pump module 60, and the intercommunication becomes possible. At this time, the identification data stored in the micro pump module 60 are read into the PC 20 via the communication device 30. The sealing member 194 being formed of an elastic silicon group rubber or the like, when the micro pump module 60 is mounted on the communication device 30, the sealing member 194 bends into an inner side of the housing, the connection terminals 97 and 98 push up the connection terminals 197 and 198 along with the sealing member 194, and the connection terminals 197 and 198 make contact with the connection terminal springs 86 and 87, thus being connected.

When the micro pump module 60 is removed from the communication device 30, the terminal connections 97 and 98 separate from the connection terminals 197 and 198, and the connection terminals 197 and 198 are returned in a direction outside the housing by the elasticity of the sealing member 194. Then, the connection between the connection terminals 197 and 198 and the connection terminal springs 86 and 87 is broken.

The reservoir 90 is placed on the top surface of the cover 41 of the communication device 30, in a condition in which it is connected to the micro pump module 60 by the tube 62 (refer to FIG. 3).

Although, in FIGS. 1 and 2, the example using the wired communication unit is shown, it also being possible to employ the wireless communication unit, it being possible to employ, as the wireless communication unit, one using an electric wave or one using an infrared ray as a communication medium, it is possible to realize the one using the electric wave by providing an antenna on the communication device 30 and the micro pump module 60, and the one using the infrared wave by providing two pairs of a light emitting element and a light receiving element, one on each of the communication device 30 and the micro pump module 60.

Continuing, a description will be given of a structure of the fluid conveyance device 50 according to the embodiment.

FIG. 3 is an exploded perspective view showing one example of the structure of the fluid conveyance device 50 of the embodiment. In. FIG. 3, the fluid conveyance device 50 is configured of, as its basic components, the micro pump module 60 and the reservoir 90.

The micro pump module 60 has the pump unit 61 and, below that, the pump drive unit 57 and the heretofore described fluid conveyance device control circuit 52 (refer to FIG. 1), stored in the housing configured of the casing 94 and the cover 95. The pump unit 57 includes a not-shown stepping motor as a drive source, and a gear train which transmits a driving force from the stepping motor to a roller base 80. In the embodiment, in order to achieve a miniaturization, a miniature stepping motor and a deceleration gear train designed for a watch are employed.

As the stepping motor, using a rotor as a bipolar magnet, rotates 180 degrees with one pulse, the roller base 80 is slowed by the gear train in such a way that it reaches a desired rotation speed. In order to obtain a desired discharge speed, or in order to optimize a rotation torque, the gear train employs a structure which can change a deceleration ratio depending on a number of teeth of gears configuring the gear train, and a combination of the teeth.

Four rollers 63 to 66 are mounted at approximately equal intervals on a periphery of the roller base 80. The rollers 63 to 66 being configured in such a way that at least one of them is capable of moving to a position in which it does not come into contact with pressing shafts 71 to 75, and a position in which it depresses them, it is in the position in which it does not come into contact when the micro pump module 60 is assembled, and moves to the position in which depression is possible in an initial drive period, to be described hereafter.

That is, the rollers 63 to 66 being in a condition in which they are not depressing the tube 62 immediately after the micro pump module 60 is assembled, during the initial drive period, they assume a condition in which they can compress the tube 62 by depressing the pressing shafts.

The tube 62 being flexible and also being a fine tube, if a specific position on the tube 62 is continually depressed by the pressing shafts in a non-driven condition, it can be supposed that the tube 62 will be permanently deformed at that position, as a result of which, it is predicted that a prescribed discharge amount will not be obtainable. As such, from the assembly until a start of driving, a condition is maintained in which the tube 62 is not compressed.

A groove being formed on an inner side of a perimeter of the casing 94, in such a way as to follow the roller base 80, the tube 62 is mounted inside the groove. The pressing shafts 71 to 75 are inserted into a wall between the heretofore described groove formed in the casing 94, and the depression in which the roller base 80 is contained. The pressing shafts 71 to 75, being disposed, from a right side direction in the figure, at approximately equal intervals in a radial pattern from a rotation axis 81 of the roller base 80, are configured in such a way as to be slidable in an axial direction.

Although the heretofore described pump unit 61 employs the structure using the rollers 63 to 66, it is also acceptable to have a structure in which a peripheral side surface of the roller base 80 is formed as a cam, and the pressing shafts 71 to 75 are press driven by the cam.

The tube 62 being a fine tube formed of an elastic olefin or the like, an outflow side extremity 62B and a receptacle connection side extremity 62A are extended in such a way as to protrude from the casing 94. An elastic, biocompatible material being employed for the tube 62, olefin is employed in the embodiment. Apart from this, it is also possible to employ a resin of the silicon group, polyethylene group or fluoride group but, depending on a kind of fluid used, it is selected bearing in mind also chemical resistance and the like.

The receptacle connection side extremity 62A of the tube 62 communicates with the reservoir 90. The tube 62 and reservoir 90 being of a structure whereby they are attachable to and removable from each other, it is possible to replace the reservoir 90, but is also possible to make the tube 62 and reservoir 90 an integrated structure which cannot be dismantled.

The reservoir 90, being a packet-shaped receptacle formed of the same material as the tube 62, is formed of a deformable thickness.

A fluid infusion portion 91 is provided in the reservoir 90. It is provided in order to insert an infusion instrument having an insertion needle (a syringe) in the fluid infusion portion 91, and inject a fluid such as the chemical liquid into the reservoir 90. When the insertion needle is removed, the fluid infusion portion 91 is sealed by its own elasticity, and an outflow of the fluid is prevented.

Then, the cover 95 is mounted on the casing 94. Although, in the embodiment, the cover 95 is screw attached with five attachment screws 96, it is possible to employ a welding attachment or adhesive attachment as an attachment structure. Apart from this, it is possible to have a structure in which packing is furnished between the cover 95 and the casing 94, and between the tube 62 and an extremity of the casing 94. In this way, an inside of the housing is sealed, and a waterproofing is provided.

In the event that it is used outside the living organism or in the atmosphere, it is not essential to have the sealed structure.

An outline shape of the micro pump module 60 being cylindrical, and corner portions being of a rounded, smooth shape, the casing 94, the cover 95 and the reservoir 90 being of a shape in which no member protrudes into the exterior, even in the hypothetic event that it is mounted inside a body of a small animal, the micro pump module 60 has a shape such as will not damage body tissue.

The casing 94 and cover 95 both being formed of a biocompatible material, the same material as the tube 62, or a material, such as a fluoride group resin, of a sufficient rigidity that it will not become deformed during the driving, being preferable, apart from these, ceramics, titanium or a titanium alloy are preferable.

Herein, a description will be given of a specific size of the fluid conveyance device 50 of the embodiment.

A diameter by thickness dimension of the micro pump module 60, and a width by length by thickness of the reservoir 90, being miniature sizes set at 20 mm×10 mm, and 10 mm×20 mm×5 mm, the tube 62 used at this time has a fluid flow portion with a diameter of 0.45 mm, and an outer diameter of 1.1 mm. Also, a capacity of the reservoir 90 being 500 µl, a discharge speed setting range is taken to be 0.5 µl/H (H stands for hour) to 15 µl/H.

Although a description has been given, in FIGS. 2 and 3, of the structure in which the micro pump module 60 and the reservoir 90 are made separate entities, it is also possible to configure the reservoir 90 integrated inside the housing of the micro pump module 60. In this case, it is preferable to configure in such a way that the fluid infusion portion 91 is caused to protrude into the casing 94 or the cover 95, and the fluid can be injected from here.

Next, a description will be given, referring to FIG. 3, of an operation of the fluid conveyance device 50.

The roller base 80, in accordance with an instruction from the drive control circuit 56, centered on the rotation axis 81, is rotated by the stepping motor in a direction of an arrow in the figure. In accordance with the rotation of the roller base 80, the rollers 63 to 66 depress the pressing shafts in order from the pressing shaft 71 on a right side extremity. At this time, the pressing shafts 71 to 75 compress the tube 62 from the reservoir 90 side, the fluid is conveyed, and discharged from the outflow side extremity 62B of the tube 62.

This kind of movement of the pressing shafts 71 to 75 being called a peristaltic motion, a pump using this peristaltic motion is called a peristaltic pump. The peristaltic pump is an optimal pump for the miniature micro pump module which can continuously convey a minute amount of fluid.

Continuing, a description will be given, referring to figures, of the inputting of the basic data and the discharge data into the PC 20, and a fluid discharge amount setting method, in the fluid conveyance system 10 of the embodiment.

Figure 4A:
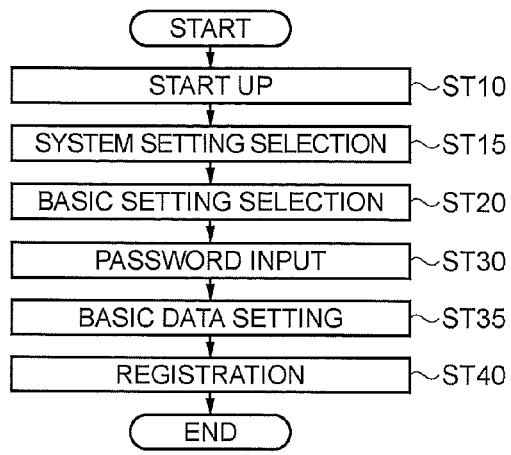
FIG. 4A is an explanatory diagram showing a flow of a manufacturer setting basic data.
Figure 4B:
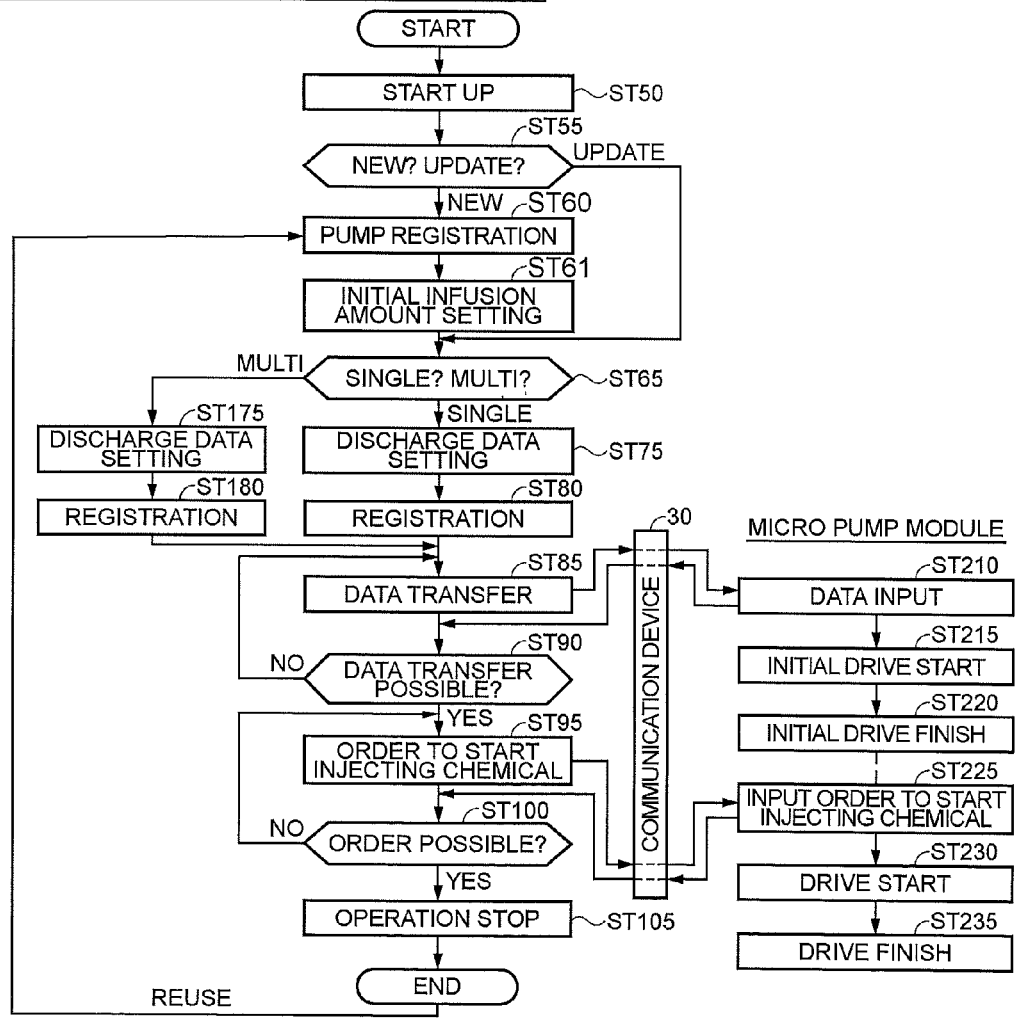
FIG. 4B is an explanatory diagram showing a flow of a user setting discharge data.

FIG. 4A and FIG. 4B are explanatory diagrams (flowcharts) showing, respectively, a flow of a basic data setting of the fluid conveyance system 10 by the manufacturer, and of a discharge data setting by the user. FIG. 1 to FIG. 3 will also be referred to when describing.

First, a description will be given of a setting operation of the basic data of the fluid conveyance system 10 by the manufacturer. The description will be given referring to screens displayed on the display 22 of the PC 20 in accompaniment to an initial setting operation. The display screens are shown individually in FIG. 5 onward. The display screens are also operation screens when setting the basic data and the discharge data.

First, the identification data such as the identification code of the micro pump module 60, a value of the correction coefficient calculated from the diameter of the tube 62 and a standard diameter, and the manufacturing date are displayed on an identification sticker, and stuck in a visible position on the micro pump module 60. At this time, the heretofore described identification data are input into the memory circuit 53 by a data-writing device (not shown).

Also, the discharge data processing device software is installed in the PC 20. The discharge data processing device software is stored in a storage medium such as the CD-ROM.

Figure 5:
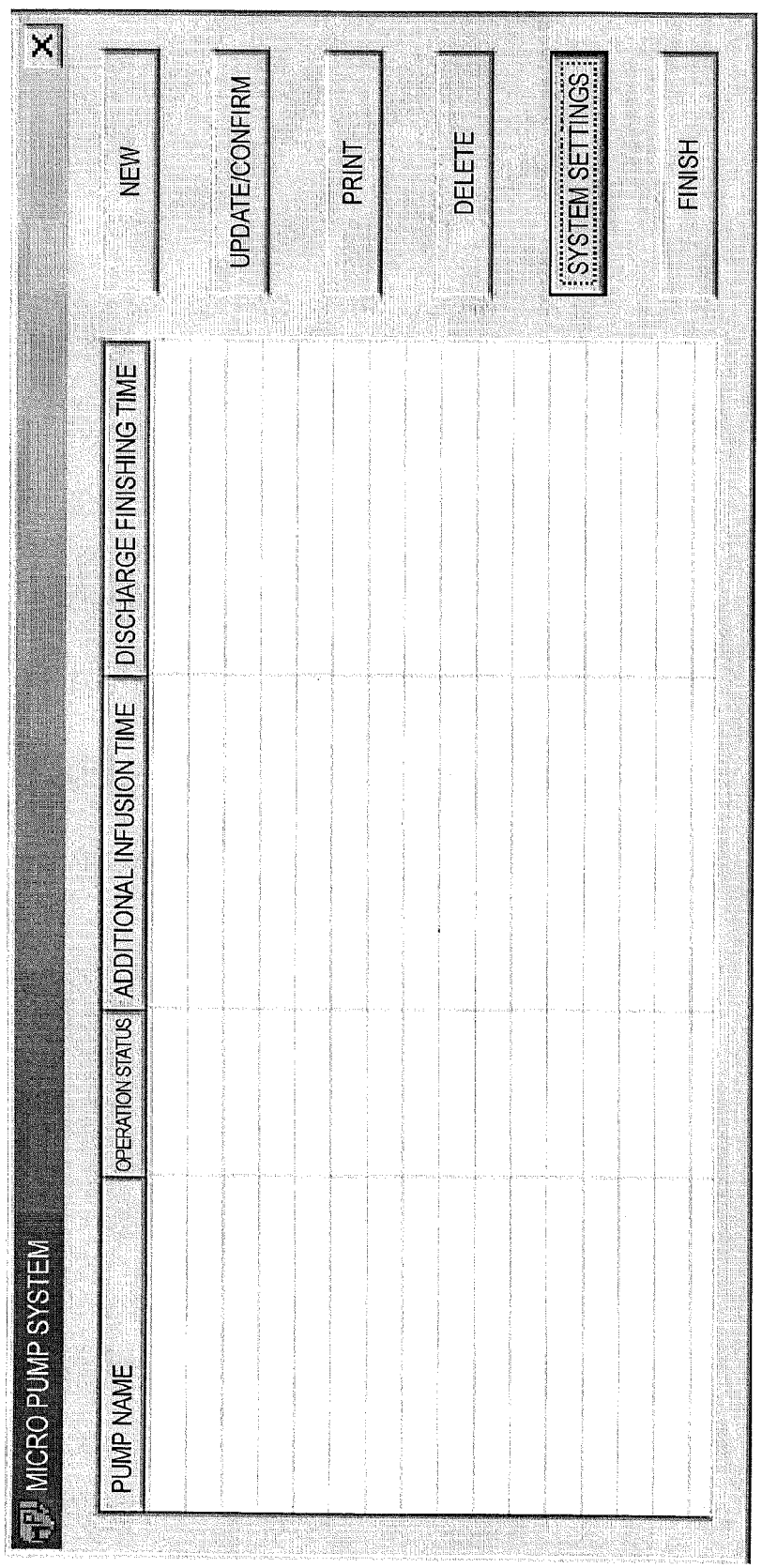
FIG. 5 is an illustration showing a display screen when a PC has been started up.

Continuing, as shown in FIG. 4A, the software is started up by operating the operating portion (the keyboard) 21 of the PC 20 (ST10). When the software is started up, a "micro pump system" screen shown in FIG. 5 is displayed in the display 22 as a start up screen. There being a list box in an area on a left side of the screen, in the event that no micro pump at all is registered, nothing is displayed.

In the event that any have already been registered, a list of the micro pump modules 60, and operating conditions etc., are displayed, as shown in FIG. 34. New, update/confirm, print, delete, system settings, and finish are displayed on function displays (which may hereafter be called buttons) being displayed.

A "New" button is selected when newly registering or additionally registering a micro pump module name, while with an "Update/Confirm" button, being a button for selecting a micro pump module name which has already been registered and is being displayed in the list box, it is possible to update setting details (which may hereafter be referred to as parameters) of the registered micro pump module.

The micro pump module name (displayed in the figure as a pump name) is the identification code of the micro pump module 60.

Also, a "Print/" button having a function for transmitting parameters of a registered micro pump module, by clicking this button after selecting a required micro pump module name from the list box, the parameters of the registered micro pump module are printed. At this time, a not-shown printer is connected to the PC 20.

A "Delete" button being used when deleting a registered micro pump module, by selecting and clicking on a micro pump module name in the list box, the micro pump module name and parameters are deleted.

A "System settings" button is used when setting a communication port and the basic data.

Figure 6:
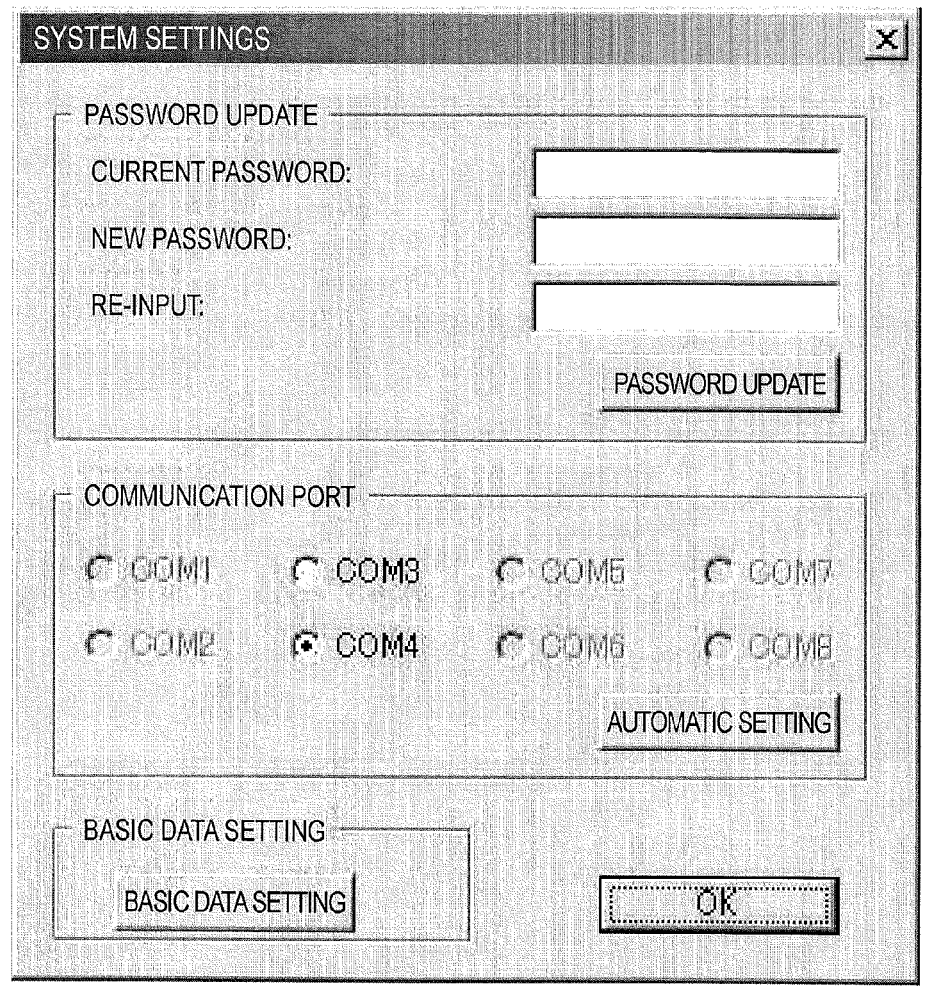
FIG. 6 is an illustration showing an initial setting screen when setting the basic data.

By selecting "System settings" on the "Micro pump system" screen (ST15), a "System settings" screen shown in FIG. 6 is displayed.

Herein, a password setting or update is carried out. Specifically, after filling in all areas "Current password", "New password" and "Input again", a "Password update" button is clicked. It is also possible to input by the same kind of operation when newly registering. For example, "MPump", set in advance as an initial password, is input, after which it is updated to a new password.

Also, when setting the "Communication port", by clicking an "Automatic setting" button, an available communication port is automatically searched for and displayed. It is also possible to manually select a required communication port.

When shifting to a basic data input, after inputting the heretofore described password and the like, a basic setting selection operation (ST20) is carried out. By clicking a "Basic data settings" button on the "System settings" screen shown in FIG. 6, a "Password" screen shown in FIG. 7 is displayed.

As function displays other than the "Basic data settings" button are functions which the user selects, they will be described hereafter in a user operation section, so the description will be omitted here.

Figure 7:
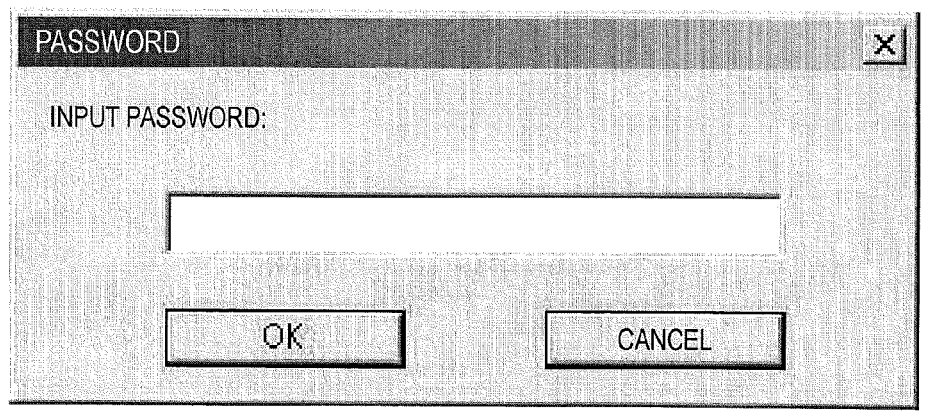
FIG. 7 is an illustration showing a password setting.

FIG. 7 shows a "Password" setting screen. Herein, a predetermined password is input (ST30). Then, by clicking an "OK" button, a "Basic data settings" screen shown in FIG. 8 is displayed.

FIG. 8 shows the "Basic data settings" screen. Herein, the basic data for driving the fluid conveyance device 50 are set in empty areas of function displays written on the display screen (ST35). That is, the basic data are a program for driving the fluid conveyance device 50 (the micro pump module 60). Pull down menu areas of the display screen, being sections in which the basic data are set step by step, indicate that a selection is to be made from therein, while optional figures are input in other empty areas.

First, a stepping motor drive pulse frequency (unit: Hz) is selected, and a micro pump discharge amount standard value (unit: μl/revolution) is input. As the correction coefficient is set by the user depending on an individual fluid conveyance device to be driven, a detailed description will be given hereafter. A correction coefficient of 1000 meaning that a diameter of a tube to be driven is the same as a value of a standard diameter of a design standard tube, in the event that a numerical value is bigger than this, it indicates that the tube diameter is bigger than the standard value, while in the event that the correction coefficient is smaller than 1000, it indicates that the tube diameter is smaller than the standard value.

A calculation method of the correction coefficient according to the embodiment will be shown hereafter. When a design value of the diameter of the fluid flow portion of the tube 62 (the standard value) is D, and an actual measurement value of a fluid flow portion diameter of the tube to be driven is d, a correction coefficient R is calculated by $R=(d/D)^2 \times 1000$. In the event that d=D, it is expressed by R=1000. The diameter means an inner diameter of a tube through which a fluid flows.

The correction coefficient may be represented by a ratio between a discharge amount of the fluid conveyance device provided with a tube to be taken as a standard and a discharge amount of the fluid conveyance device to be driven.

A "micro pump discharge amount (unit: μl/revolution)" is calculated as a product of the heretofore described micro pump discharge amount standard value and the correction coefficient, and displayed. Also, a "Maximum discharge speed upper limit value (unit: μl/H, H stands for hour)" is set by the manufacturer from a maximum allowable current of a battery used, in the event that it is necessary to add a limit.

When driving the fluid conveyance device 50, it can be supposed that the fluid will evaporate from the tube 62 or the reservoir 90. In the fluid conveyance device 50 of the embodiment, which discharges a minute amount in microliter (μl) units, this evaporation amount cannot be ignored. Thus, it can be supposed that a sufficient discharge amount cannot be obtained when setting the discharge speed at will. Consequently, by carrying out a setting of a "Minimum setting discharge speed (unit: μl/H)" as a lower limit value of the discharge speed, a desired fluid conveyance amount is assured.

Also, a "Maximum discharge time upper limit value (unit: H)" is set. This is a specification which, although it is possible to continue the driving of the fluid conveyance device 50 over a long period of time in the event that the discharge amount is small with respect to the capacity of the reservoir 90, in order to increase a reliability, sets the upper limit value of the maximum discharge time, and stops the driving at a point at which the set time has elapsed.

Also, an "Initial drive speed (unit: μl/H)" and an "Initial drive time (unit: s, where s stands for second)" are set as basic data of the drive conditions in the initial drive period. A "Stepping motor pulse width (unit: ms)" is set to suit drive characteristics of the stepping motor.

A "Stepping motor deceleration ratio", which indicates a deceleration ratio of the gear train, being a factor for calculating a rotation speed of the roller base with respect to a drive frequency, that is, a rotation speed, of the stepping motor, is set because it is possible to change the combination of the gear train, and switch the deceleration ratio. Sections "Battery capacity", "Safety rate", "Stepping motor consumption current (unit: μA/Step)", and "CPU (Central Processing Unit) execution time consumption current (unit: μA)" are sections which serve as standards for a setting of the drive time.

The safety rate is set assuming a fluctuation of a remaining capacity, with respect to a standard battery capacity (unit: mAH). Also, in the CPU execution time consumption current (unit: μA), a consumption current when driving is input, while in a case of a "CPU halt time consumption current (unit: μA)", as one portion of the CPU (the fluid conveyance device control circuit 52) also drives before the fluid conveyance device 50 starts driving, a consumption current at that time is input.

In the embodiment, a power source voltage detection circuit (SVD) being built into the drive control circuit 56, it detects the voltage of the battery 58 as the power source. First, the "power source voltage detection circuit (SVD)" is switched to ON or OFF and, when selecting ON, a "power source voltage detection circuit (SVD) detection interval (unit: min, where min stands for minute)" is selected from setting values, and a "power source voltage detection circuit (SVD) detection voltage (unit: V)" is selected from setting values. In FIG. 8, the detection voltage is exemplified as 1.22V. The detection voltage is a threshold voltage for stopping the drive of the micro pump module 60 when the battery voltage drops to 1.22V or less.

Next, the "Reservoir capacity (unit: µl)" and a "Reservoir lower limit capacity (unit: µl)" are set. The reservoir capacity is a capacity of the fluid injected. As it is difficult, when discharging the fluid, to discharge fluid equivalent to 100% of the previously described reservoir capacity, there being a slight discharge residue, a manageable effective capacity is set in the reservoir lower limit capacity.

Then, an "Operating mode" is set. The operating mode is selected from "Normal" or "Test". "Normal" indicates that it is not possible to reuse the micro pump module 60, while "Test" indicates that it is possible to reuse the micro pump module 60.

Continuing, a "Setting discharge speed correction (evaporation) (unit: µl)" and an "Infusion amount correction (evaporation) (unit: µl)" are set. The setting discharge speed correction is a correction value which takes into account the evaporation amount of the fluid from the tube 62 or the reservoir 90. That is, in the event that the evaporation of the fluid exists, as the discharge amount will be insufficient at a design value of the discharge speed, the design discharge speed is corrected.

Also, the infusion amount correction, taking into account the heretofore described evaporation, subtracts an infusion amount correction value from a fluid amount injected into the reservoir 90 by the user, and calculates an actual infusion capacity, that is, a prescribed infusion amount.

On inputting all of the heretofore described basic data into the PC 20, and clicking a "Register" button, the basic data are written into the discharge data processing device software (ST40). Consequently, the basic data being written on the CD-ROM on which the discharge data processing device software is written, the CD-ROM is handed over to the user along with the fluid conveyance device 50 corresponding to the basic data which is written.

Also, it is also acceptable to hand the PC 20 itself in which the discharge data processing device software and the basic data are written, over to the user.

At this time, the reservoir 90 is handed over to the user in a condition in which it is mounted on the micro pump module 60, and the user injects the fluid such as the chemical liquid into the reservoir 90. Alternatively, it is also possible that the reservoir 90 is supplied to the user as a separate entity, the user injects the chemical liquid or the like into the reservoir 90, and mounts it on the micro pump module 60.

Continuing, a description will be given, referring to the drawings, of a setting and input by the user of the identification data and the discharge data into the fluid conveyance device 50, after the heretofore described basic data has been input, and of a drive method thereof. FIG. 1 to FIG. 3 will also be referred to.

FIG. 4B is an explanatory diagram showing a flow of the setting input by the user of the discharge data into the PC 20, and of the drive of the micro pump module 60.

First, the user inserts the CD-ROM supplied by the manufacturer, on which the discharge data processing device software and the basic data are written, into the PC 20, and starts up the discharge data processing device software (ST50). At this time, the USB cable 39 is connected to the communication device 30 (refer to FIG. 1).

Figure 10:
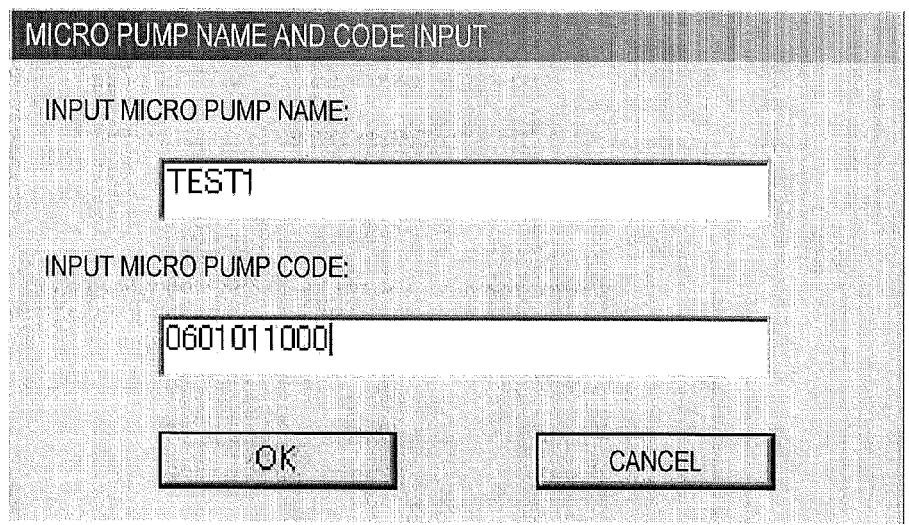
FIG. 10 is an illustration showing a condition in which the micro pump name and code have been input.

On starting up the discharge data processing device software, the "Micro pump system" screen shown in FIG. 5 is displayed as the start up screen. Herein, the user selects whether to newly register, or to update, the discharge data (ST55). If "New" is selected, a "Micro pump name & code input" screen shown in FIG. 10 is displayed. Details displayed on the "Micro pump name & code input" screen are the identification data. A "Name of the micro pump" on the screen being the identification code (displayed as TEST 1), a "Micro pump code" represents the manufacturing period and the correction coefficient. An exemplified numerical sequence of 0601011000 indicates that the manufacturing period is 060101. That is, it represents Jan. 1, 2006. Also, a suffix of 1000 represents the correction coefficient. These identification data, being input in advance into the memory circuit 53 of the micro pump module 60, are automatically written into the PC 20 when the PC 20, the communication device 30 and the fluid conveyance device 50 are connected.

The "Update/Confirm" button, being a button for selecting a micro pump module name which has already been registered, and is being displayed in the list box, updates setting details of the registered micro pump module.

By comparing the identification data displayed on the display screen, and the identification data displayed on the identification sticker, it is possible to increase the reliability of the data.

Figure 9:
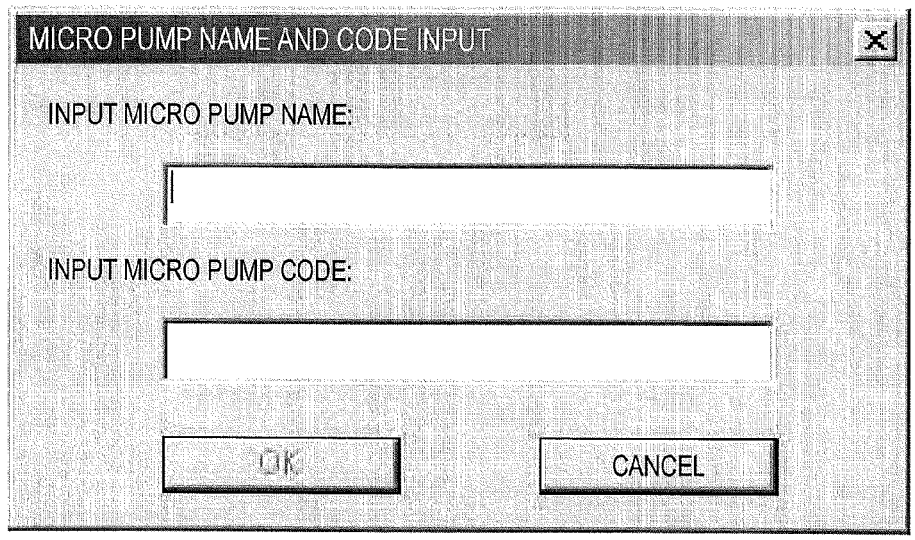
FIG. 9 is an illustration showing an operation newly setting a micro pump name and code.

It is conceivable that the identification data input in the memory circuit 53 could be deleted by an environmental burden, such as static electricity, during conveyance or the like. In this kind of case, as shown in FIG. 9, the identification data area is blank, or there is a display differing from the identification data. At this time, it is possible to operate the PC 20, and input the identification data displayed on the identification sticker into the relevant micro pump module 60.

In the event that the identification data input in advance into the micro pump module at a time of manufacturing should be deleted, it is possible to input the identification data from the discharge data processing device 20.

Figure 11:
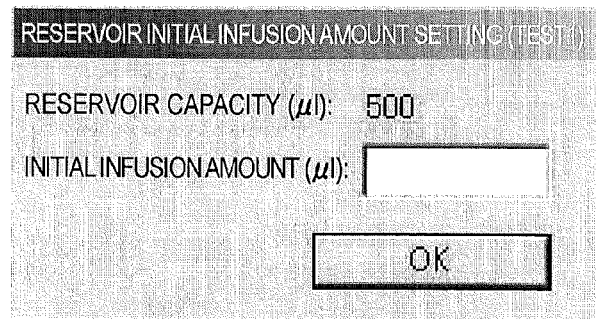
FIG. 11 is an illustration showing an input of an initial infusion amount of a chemical liquid in a reservoir.

On registering the micro pump name and code (ST60), and clicking an "OK" button, a "Reservoir initial infusion amount setting" screen shown in FIG. 11 is displayed.

Herein, an initial infusion amount is set (ST61). As the initial infusion amount sets an amount injected when first driving, it is not possible to set a capacity which exceeds the reservoir capacity which the manufacturer has set as the basic data (shown as 500 µl). On clicking an "OK" button on this screen, a "Micro pump control" screen and a "Discharge progress plan graph" screen, shown in FIG. 12 and FIG. 13, are displayed on the same display screen.

Figure 13:
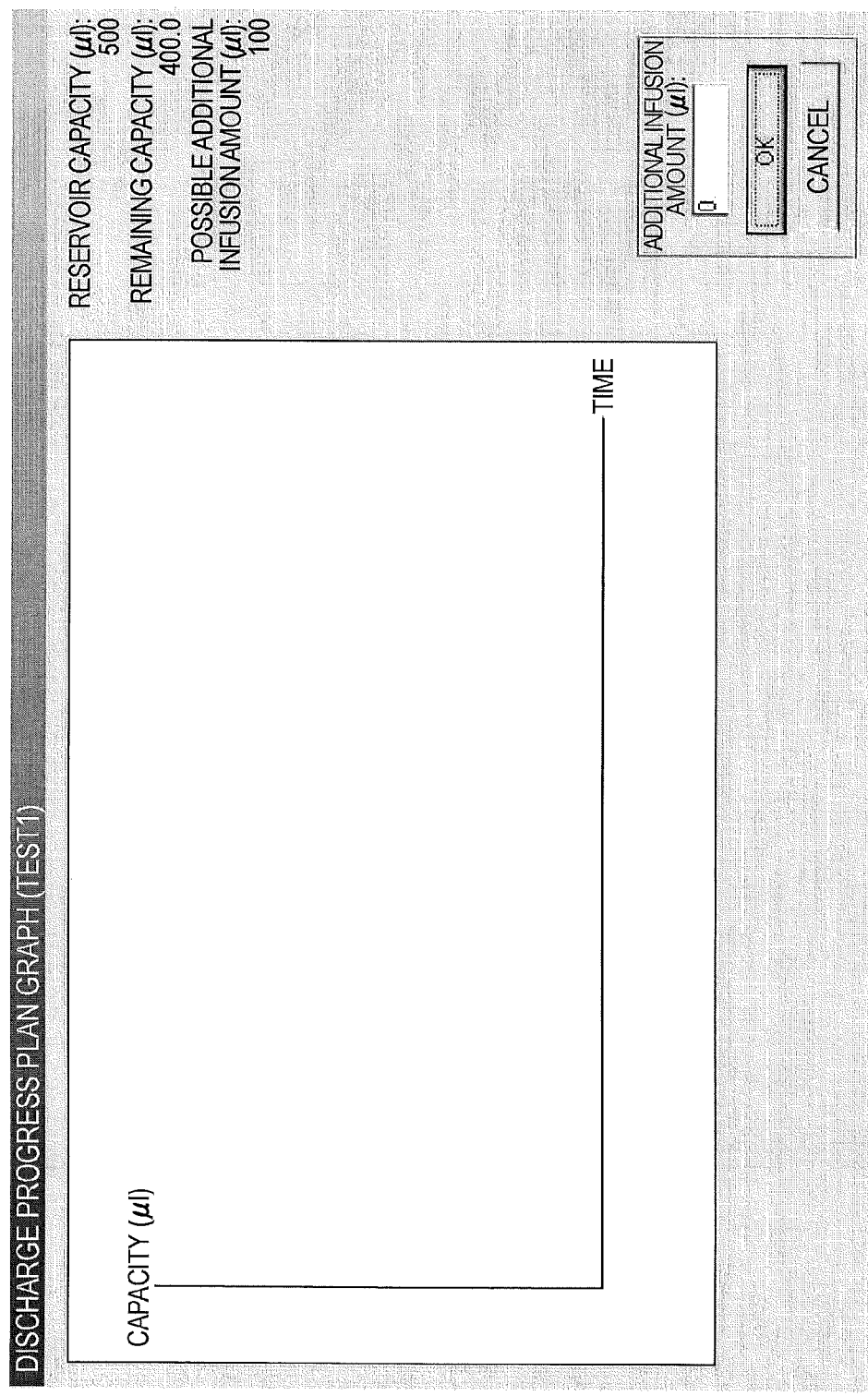
FIG. 13 is a discharge progress plan graph showing a discharge capacity and a discharge time.

As the discharge progress plan graph shown in FIG. 13 is a graph showing a relationship between a set drive time and a discharge amount, the graph is not yet being displayed at this point.

Figure 12:
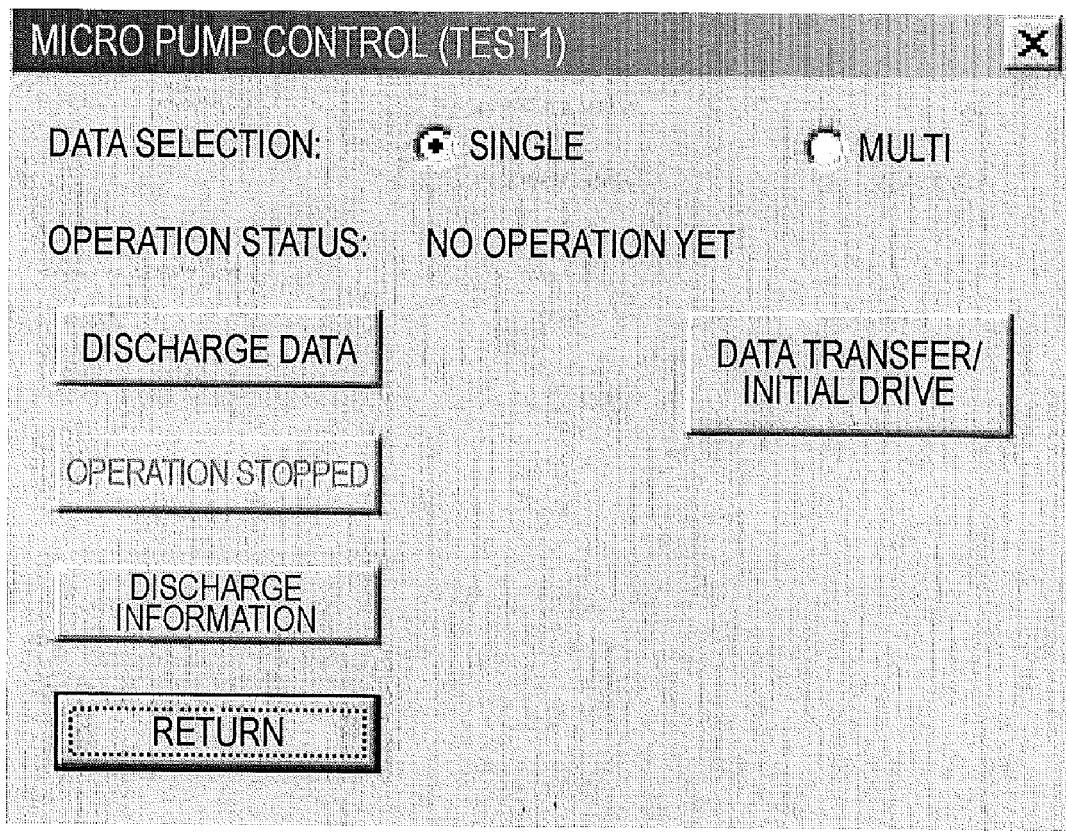
FIG. 12 is an illustration showing a selection of a single drive or a multi-drive.

In FIG. 12, a selection is made as to whether the drive of the micro pump module in a "Data selection" area is a single specification (expressed as single or single drive) or a multiple specification (expressed as multi or multi-drive) (ST65). Herein, "single" represents driving based on one set of discharge data for one micro pump module, while "multi" represents driving based on a plurality of discharge data for one micro pump module.

First, a description will be given of a discharge data setting flow in a case of selecting "single". A "discharge data" button on the screen shown in FIG. 12 is clicked.

On clicking on "Discharge data/", a "Discharge data setting: single" screen shown in FIG. 14 is displayed. In FIG. 14, sections other than the previously described basic data are blank. Herein, a discharge setting speed and a discharge time are set (ST75). A condition in which the discharge data have been set is shown in FIG. 15.

A description will be added of the discharge data set on this screen. A "Maximum settable discharge speed (unit: μl/H)" is a value calculated from the previously described basic data input by the manufacturer. The user, first, inputs a discharge speed necessary for actually driving in a "Discharge speed setting (unit: μl/H)" area. In the event that a number is input for this discharge speed which exceeds the maximum discharge speed, "Error" is displayed.

A "Maximum settable discharge time (unit: time H)" being a value calculated from the battery capacity, safety rate and total consumption current input as the basic data, and a "Maximum discharge amount (unit: μl)" being a value calculated from a product of the previously described maximum discharge speed and maximum discharge time, they are calculated by a calculation device of the PC 20.

Next, a prescribed discharge time (drive time) is set in a "Discharge time setting (unit: H)" area. As "Error" is displayed in the event that this value is set in excess of the maximum discharge time, a resetting is carried out.

A "Set discharge amount (unit: μl)" is a value calculated from the discharge speed and the discharge time. That is, it is calculated by (discharge speed×discharge time).

Figure 16:
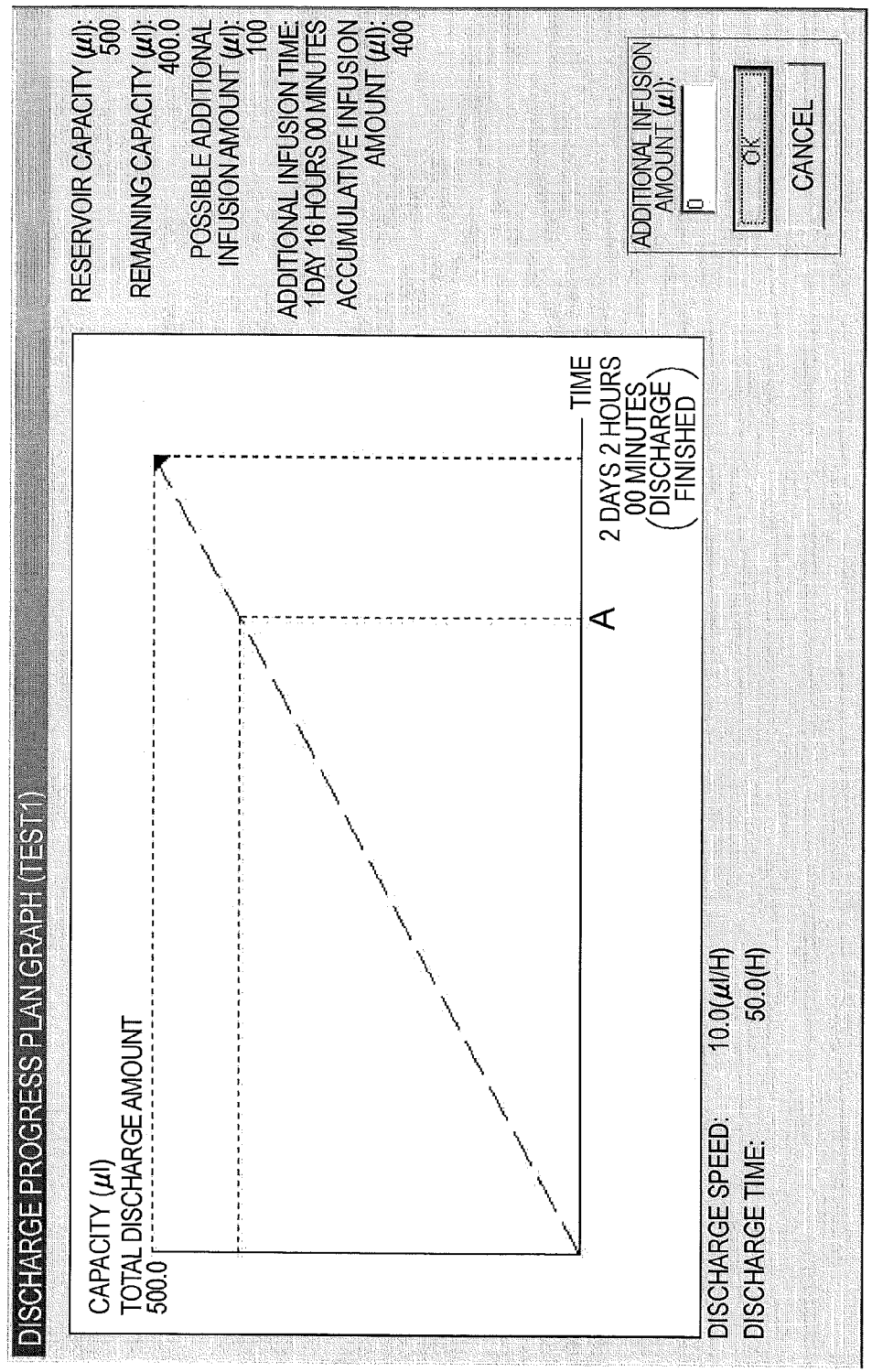
FIG. 16 is a discharge progress plan graph showing a relationship between the set discharge capacity and discharge time.

After inputting these discharge data, a "Register" button is clicked, and the discharge data is registered (ST80). On clicking the "Register" button, returning to the "Micro pump control" screen shown in FIG. 12, a "Discharge progress plan graph" screen shown in FIG. 16 is displayed.

The basic data, and the discharge data which the user has set, being displayed on the discharge progress plan graph, as regards the graph, the discharge time (discharge elapsed time) is displayed on a horizontal axis, and a total discharge amount on a vertical axis. A position indicated by reference character A shows an additional infusion time. A detailed description will be given hereafter of the additional infusion time.

Figure 17:
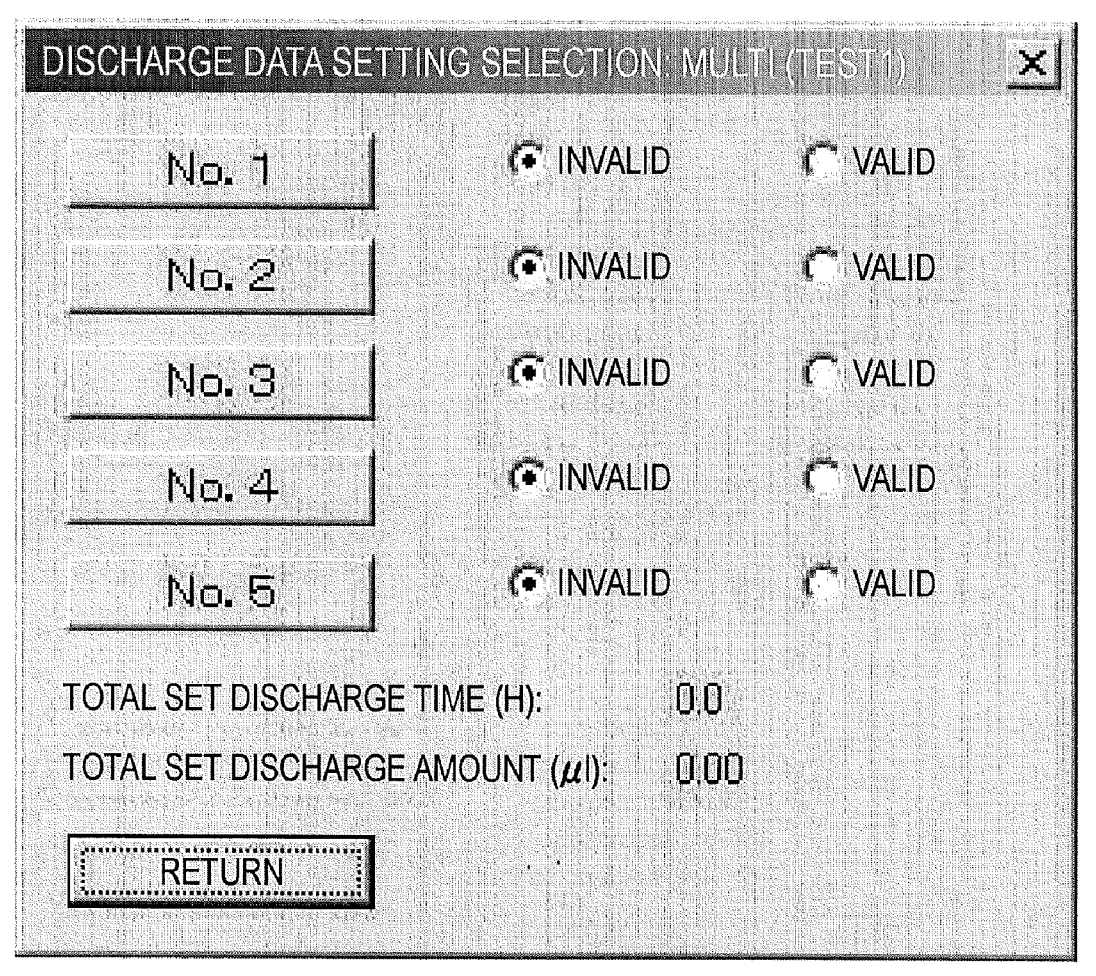

Next, a description will be given of the multi-drive. On selecting "multi" in ST65 (on the "micro pump control" screen shown in FIG. 12), and clicking on "Discharge data", a "Discharge data setting selection: multi" screen shown in FIG. 17 is displayed. The multi discharge data are set on this screen.

FIG. 17 indicating that five kinds of condition setting, No. 1 to No. 5, are possible, a multi-drive discharge data setting is carried out (ST175). As no discharge data have been input at this point, "Invalid" is displayed for all of them. Assuming that No. 1 is selected and clicked on, a shift is made to a "Discharge data setting: multi No. 1" screen of the micro pump name No. 1 shown in FIG. 18.

Then, the discharge speed setting and the discharge time setting are carried out sequentially. Herein, values within ranges of the maximum settable discharge speed and maximum settable discharge time, set as the basic data, can be input. A screen on which the heretofore described discharge data have been input is exemplified in FIG. 19. Next, by clicking a "Register" button, the No. 1 data are registered (ST180). After being registered, returning to the "Discharge data setting: multi" screen (FIG. 17), No. 1 is displayed as "Valid", as shown in FIG. 20.

In this way, the discharge data are set (input) sequentially for No. 1 to No. 5. A condition in which the discharge data have been input for No. 1 to No. 5 is shown in FIG. 21. That is, "Valid" is displayed for all of No. 1 to No. 5. On clicking a "Return" button from this condition, a "Micro pump control" screen shown in FIG. 22, and a "Discharge progress plan graph" screen shown in FIG. 23, are displayed on the same screen.

Figure 22:
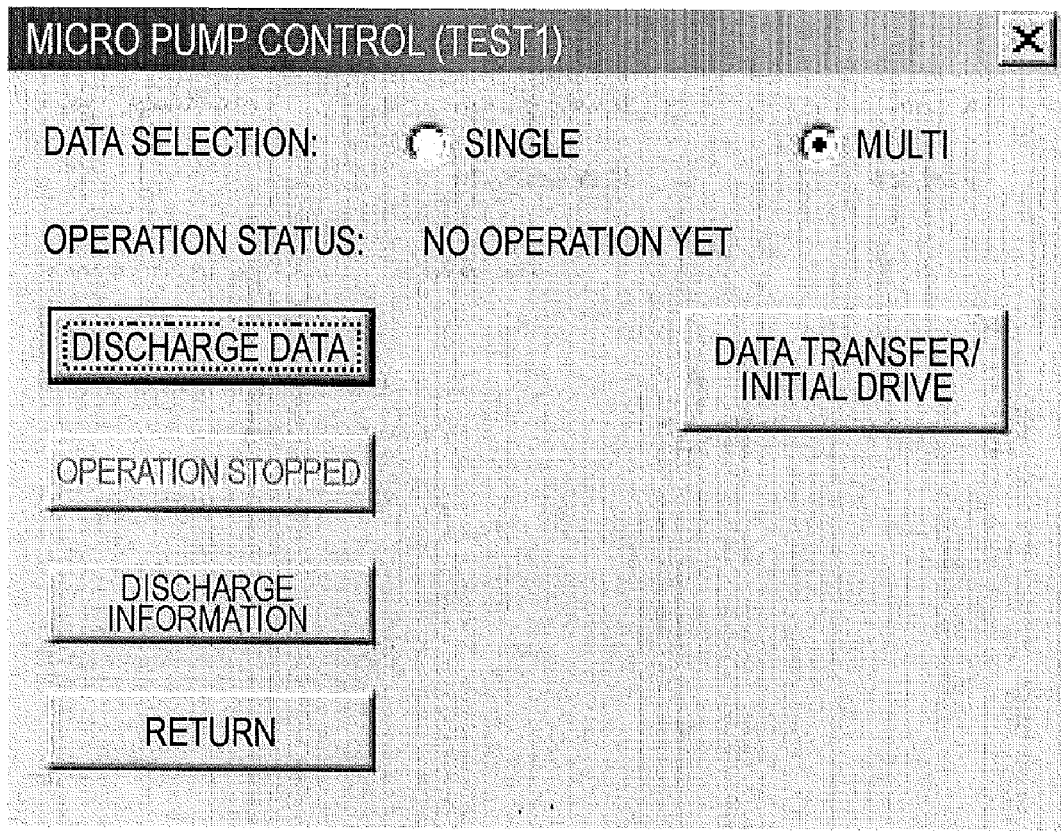
FIG. 22 is an illustration showing a "Micro pump control" screen during the multi-drive.
Figure 23:
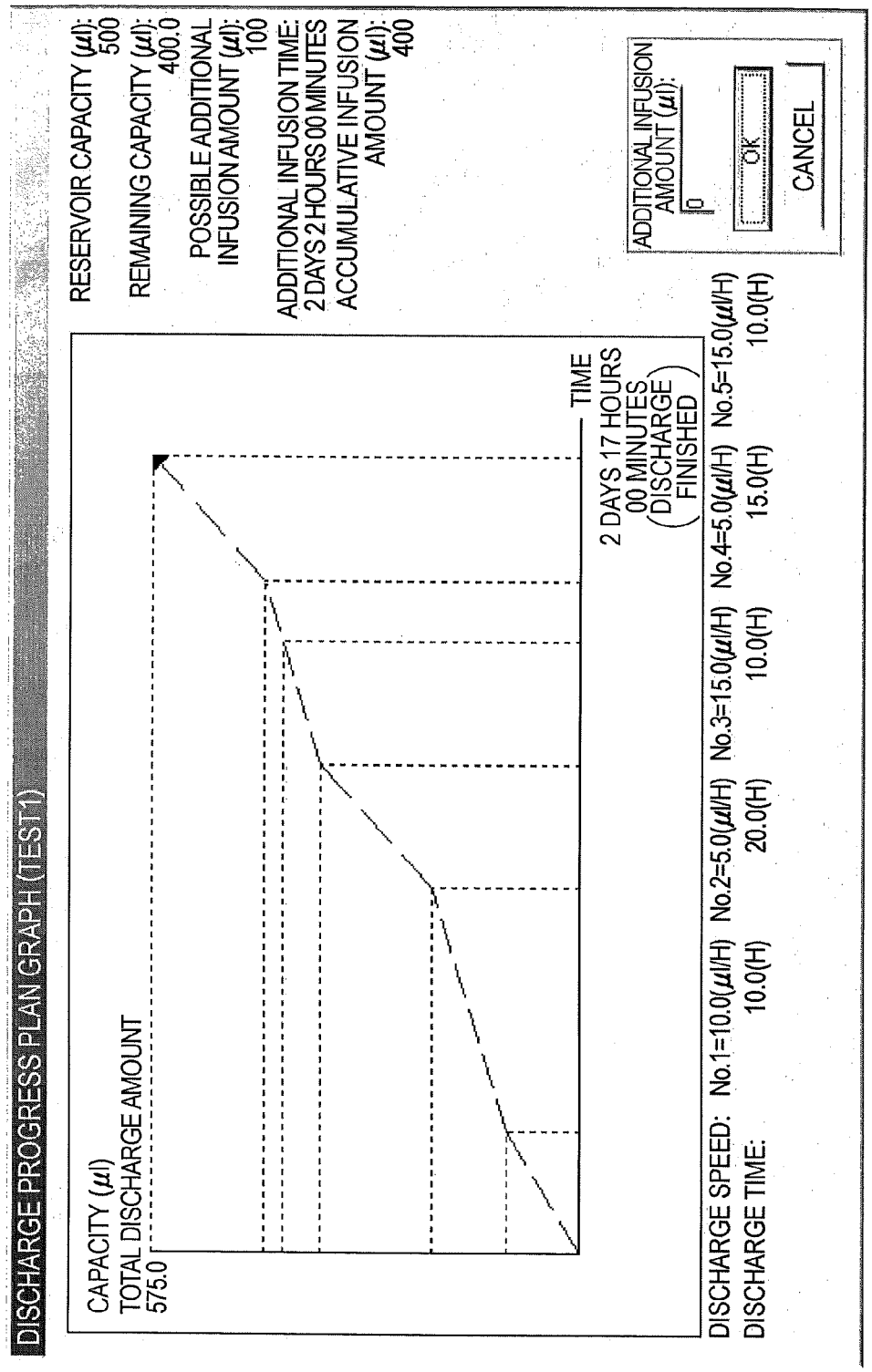
FIG. 23 is a discharge progress plan graph showing a relationship between the set discharge capacity and the discharge speed during the multi-drive.

Although "multi" is being displayed in FIG. 22, as there is not yet any drive, "No operation yet" is displayed in an "Operation status" area. Also, in FIG. 23, results of the relationship between the discharge time and the total discharge amount, based on the five kinds of discharge data, calculated by the calculation device of the PC 20 are displayed on a graph. That is, a graph is displayed which shows five kinds of discharge speed between the discharge start and the discharge finish.

Continuing, the registered discharge data are transferred to the micro pump module 60 via the communication device 30 (ST85). The transfer of the discharge data is carried out in the same way for both the single drive and the multi-drive. First, the micro pump module 60 is mounted in the prescribed position on the communication device 30. The connection terminals 97 and 98 are connected respectively to the connection terminals 197 and 198, and the intercommunication between the communication device 30 and the micro pump module 60 is established.

Figure 24:
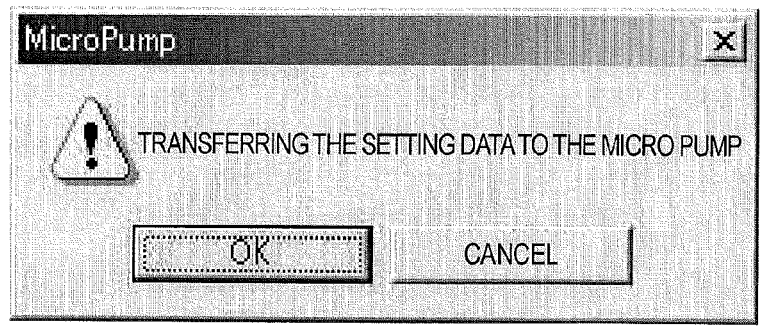
FIG. 24 is an illustration showing a transfer operation of the set discharge data to the fluid conveyance device.

On clicking on "Data transfer/initial drive" on the "Micro pump control" screen shown in FIG. 22, a shift is made to a screen saying "Transferring setting data to the micro pump" shown in FIG. 24. At this point, an "OK" button is clicked, transferring the basic data and the discharge data to the micro pump module 60. Herein, on confirming that the input basic data and discharge data have been input with the prescribed details, a "Complete data input signal" is transmitted to the PC 20 via the communication device 30 (ST210).

Figure 25:
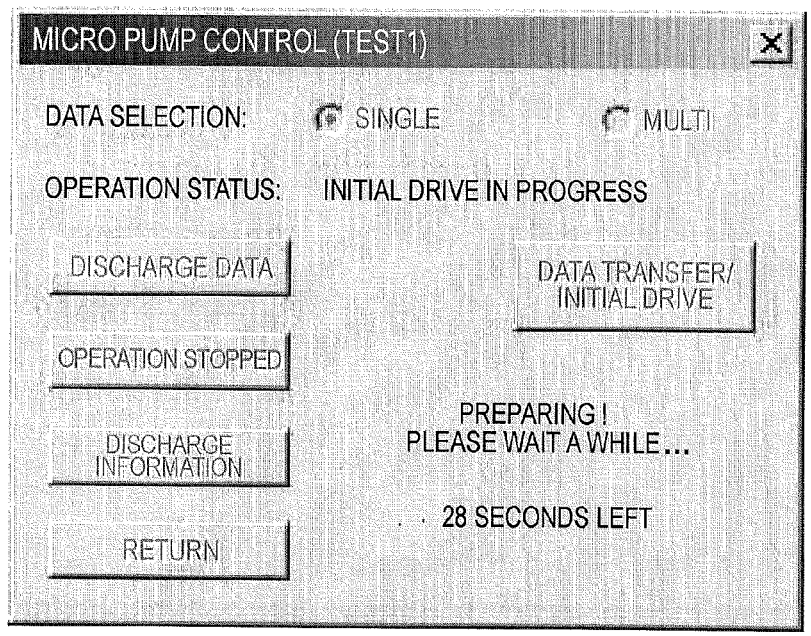
FIG. 25 is an illustration showing a condition during an initial drive of the fluid conveyance device.

On the prescribed data being transferred, the micro pump module 60 automatically starts the initial drive (ST215) A "Micro pump control" screen shown in FIG. 25 is displayed on the display screen. "Initial drive in progress" is displayed as the operation status.

A possibility or otherwise of the data transfer is determined in the PC 20 (ST90). If the input completion signal is not received within a prescribed time, it is judged that the data transfer has failed, and the "Data transfer" operation (ST85) is carried out again. If the data are not transferred normally, a display saying "An error has occurred while transferring the setting data to the micro pump", shown in FIG. 26, appears.

Figure 27:
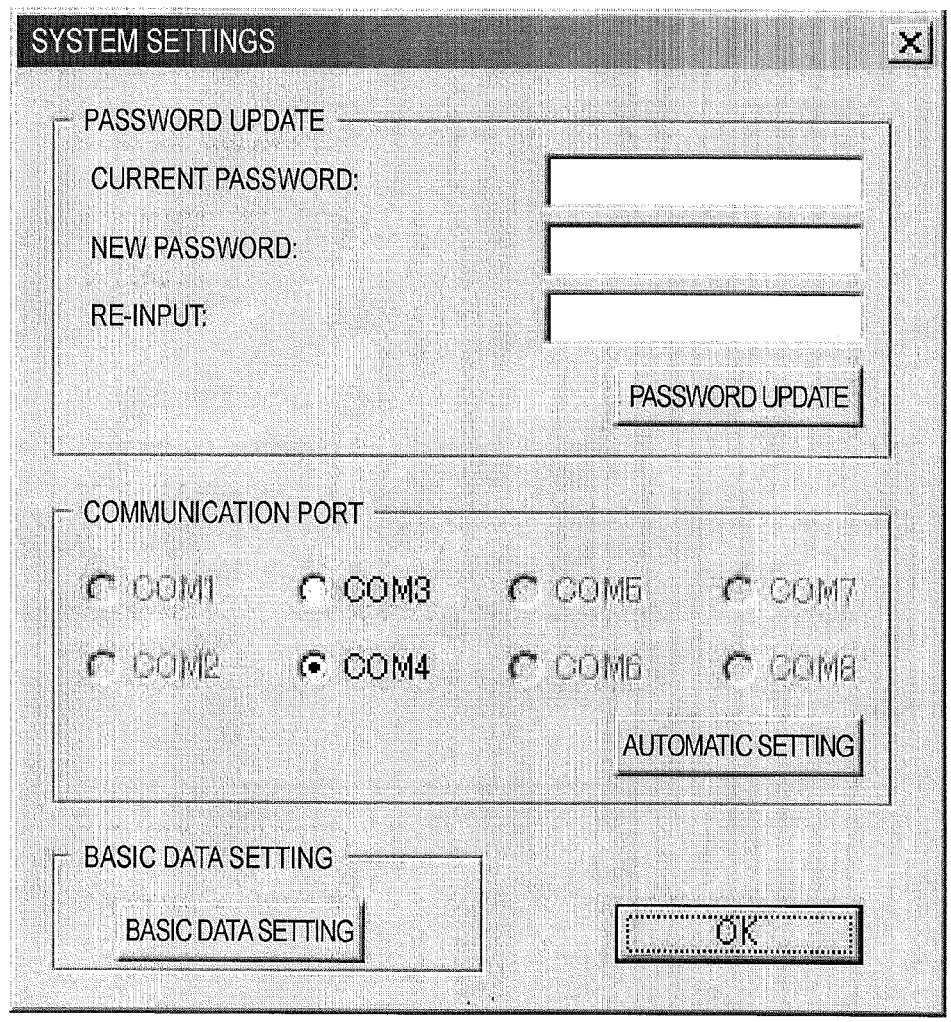
FIG. 27 is an illustration showing an operation selecting a communication port when the transfer of the discharge data has failed.

Herein, on clicking on "OK", returning to the "Micro pump control" screen shown in FIG. 25, the data transfer operation is carried out again. In the event that there is a further failure in the data transfer, "Return" is clicked on, and a valid port is changed in a "Communication port" area on a "System settings" screen shown in FIG. 27.

On the data being input into the micro pump module 60, the micro pump module 60 starts the initial drive (ST215) and, after driving for a certain time based on the input basic data and discharge data, finishes the drive (ST220). The initial drive period, being set in advance by the basic data, as previously described, is set as a time from the micro pump module 60 starting the initial drive until a condition in which the fluid can be stably discharged.

The "Micro pump control" screen shown in FIG. 25 being displayed on the PC 20 while the initial drive is being carried out, "Initial operation in progress" is displayed during the initial drive, and a remaining initial drive time is displayed (28 seconds left is shown on the screen). On the initial drive finishing, a screen saying "Do you want to start injecting the chemical?", shown in FIG. 28, is displayed.

Herein, if "Yes (Y)" is clicked, an order to start injecting the chemical is transmitted from the PC 20 (ST95). The order to start injecting the chemical is transferred to the micro pump module 60 through the communication device 30. The micro pump module 60, on the order to start injecting the chemical being input (ST225), inputs an "Order input completion signal" into the PC 20.

Figure 26:
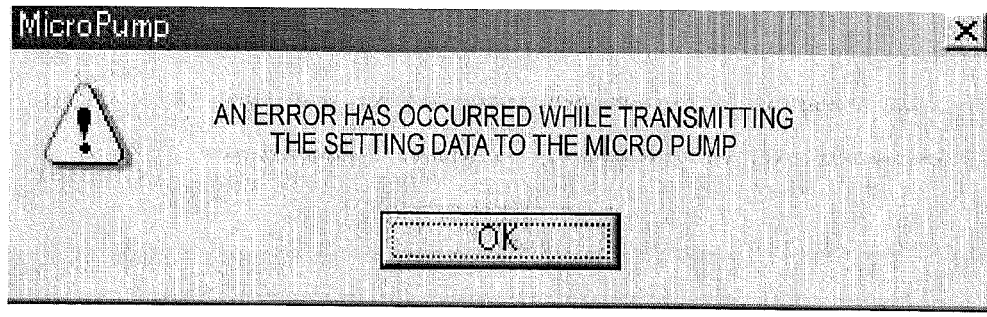
FIG. 26 is an illustration showing a condition when the transfer of the discharge data has failed.

The PC 20 determines whether the order to start injecting the chemical has been transferred to the micro pump module 60 (ST100) and, if the order input completion signal has been received, waits until the drive of the micro pump module has finished. If the data transfer has failed, the screen shown in FIG. 26 is displayed, an "OK" button is clicked, and the data transfer operation is carried out again by the previously described kind of procedure.

Figure 28:
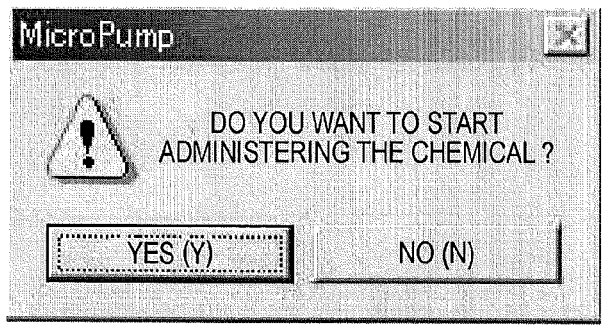
FIG. 28 is an illustration showing an order to start an injection of a chemical.
Figure 29:
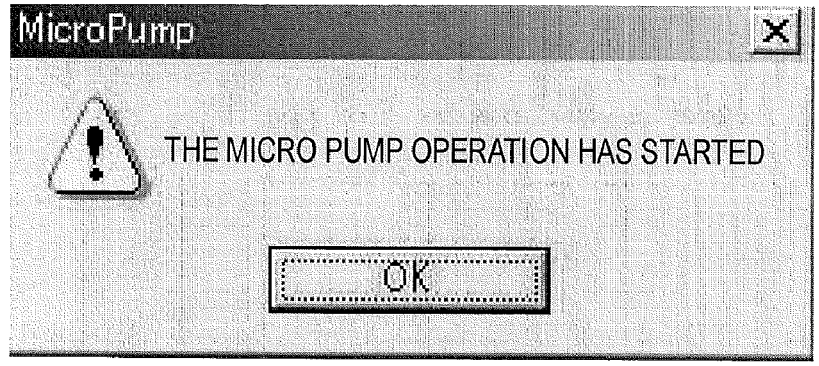
FIG. 29 is an illustration showing an operation confirming the order to start the injection of the chemical.

If "Yes (Y)" is selected on the screen of FIG. 28, a "The micro pump operation has started" screen shown in FIG. 29 is displayed. On clicking "OK" at this point, a "Micro pump control" screen and a "Discharge progress graph" screen, shown in FIG. 30 and FIG. 31 respectively, are displayed.

Figure 30:
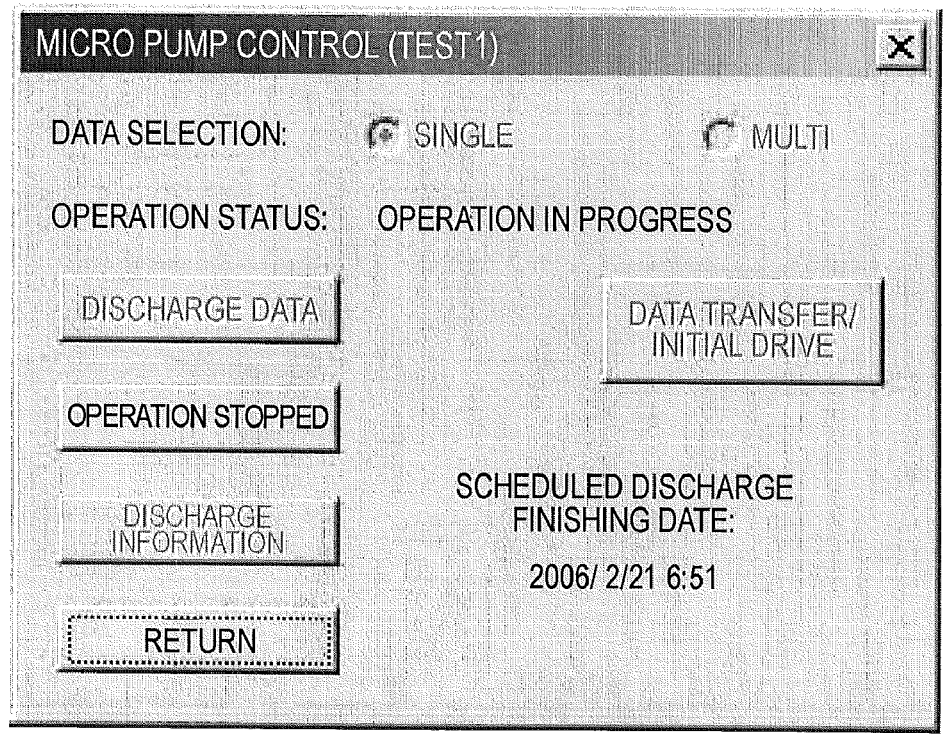
FIG. 30 is an illustration showing conditions under which the drive of the fluid conveyance device has been started.

The micro pump module 60 starts the drive when the order to start injecting the chemical has been input (ST230) The operation status is displayed as "Operation in progress" on the "Micro pump control" screen of FIG. 30.

Figure 31:
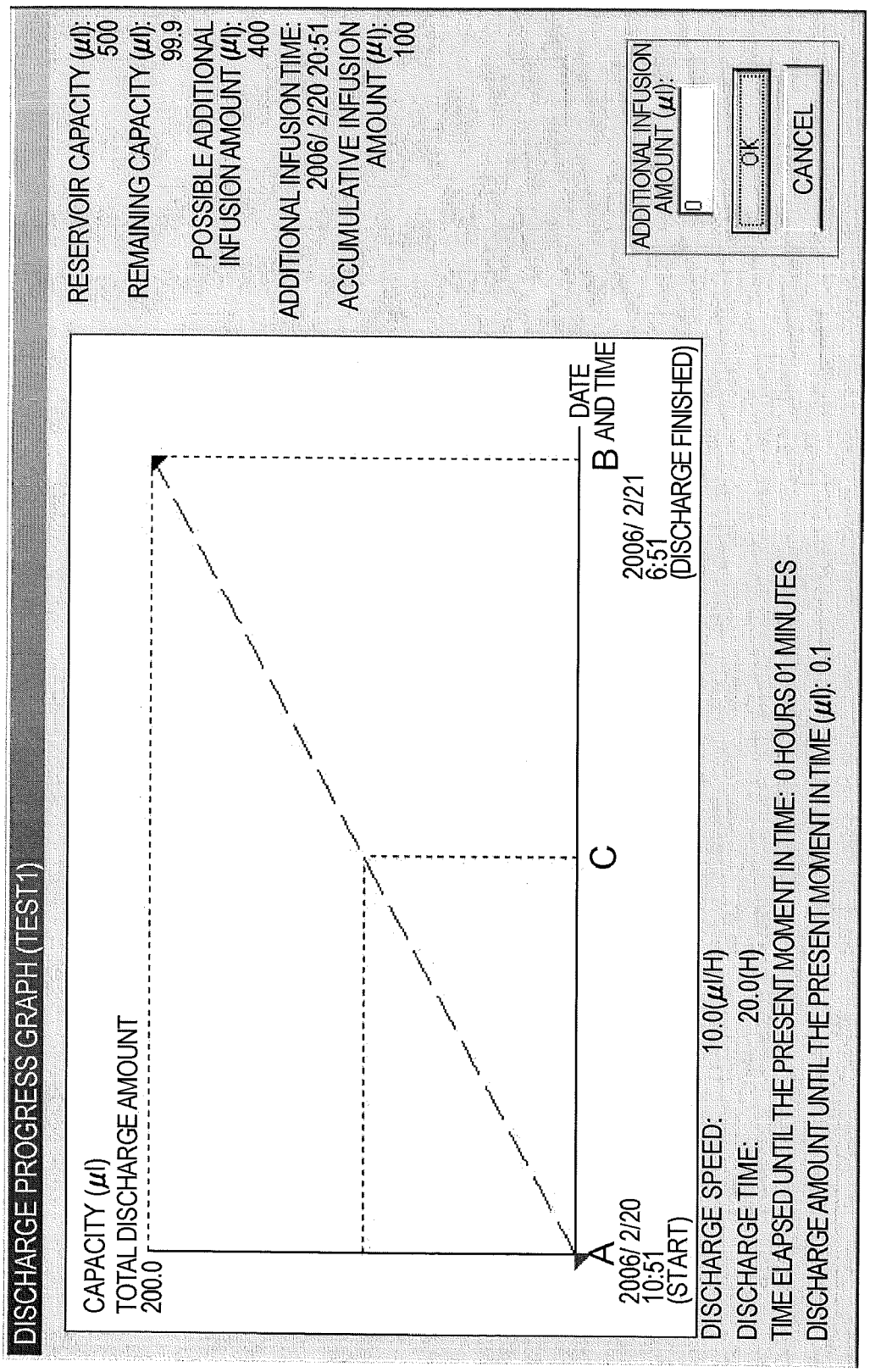
FIG. 31 is a discharge progress graph showing drive conditions of the fluid conveyance device.

The "Discharge progress graph" screen of FIG. 31 representing the case of the single drive, a position of reference character A indicates a discharge starting time (the total discharge amount), and a position of reference character B a discharge finishing time (the total discharge amount). A position of reference character C represents an additional infusion time (also indicating an accumulative infusion amount) of the fluid, to be described hereafter.

Figure 32:
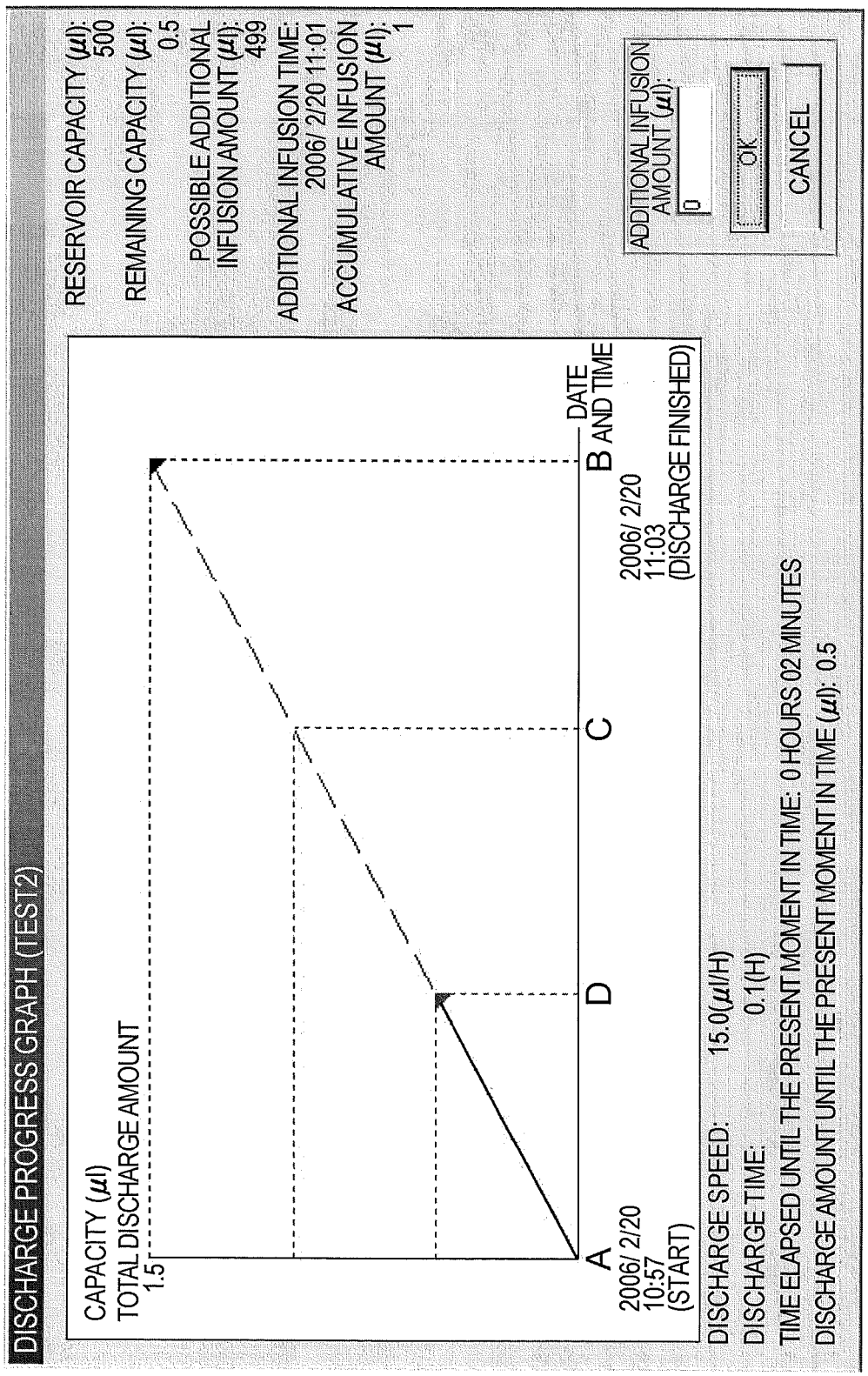
FIG. 32 is a discharge progress graph showing drive conditions of the fluid conveyance device at the present moment during the single drive.

Then, a discharge status from the discharge start until the present point in time is displayed on a "Discharge progress graph" screen shown in FIG. 32. That is, a position of reference character D indicating the present time, FIG. 32 shows that an elapsed time is 0 hours 2 minutes, and a discharge amount until the present point in time is 0.5 µl.

Figure 33:
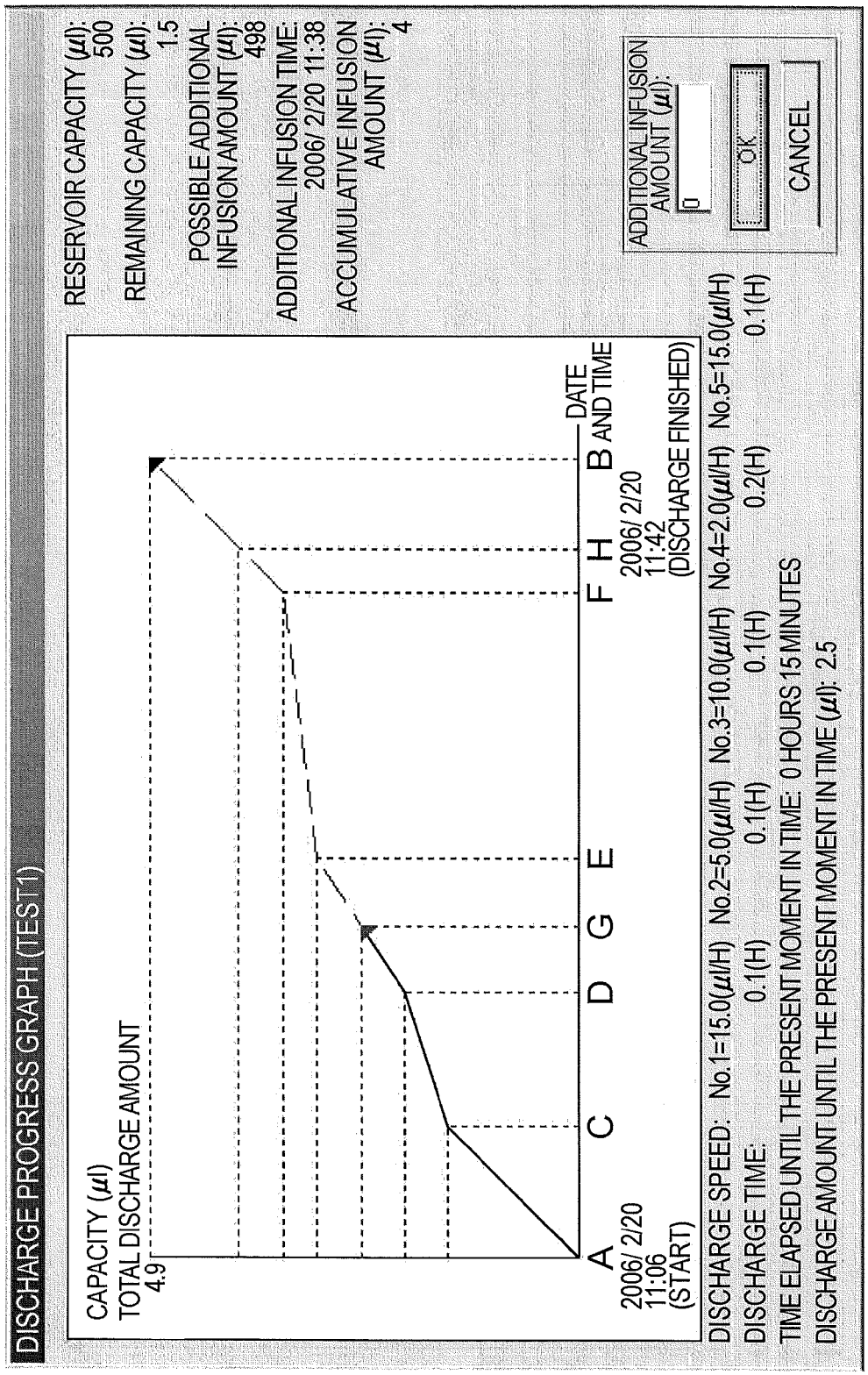
FIG. 33 is a discharge progress graph showing drive conditions of the fluid conveyance device at the present moment during the multi-drive.

A discharge status in the case of the multi-drive is represented in a "Discharge progress graph" shown in FIG. 33. According to this graph, the five kinds of discharge condition are set. That is, it is indicated that each of the discharge conditions No. 1 to No. 5 can be switched in each of positions of reference characters C to F.

Then, a position indicated by reference character G, indicating the present time, shows that a time elapsed from the discharge starting time (reference character A) until the present point in time is 0 hours 15 minutes, and a discharge amount until the present point in time is 2.5 µl. Then, the drive is continued until the discharge finishing time indicated by reference character B.

A position of reference character H represents the additional infusion time (the accumulative infusion amount), to be described hereafter.

When the fluid conveyance device 50 has started the drive (ST230), the fluid conveyance device 50 is swiftly mounted on a mounting subject. For example, the fluid conveyance device 50 is embedded in a living organism such as a small animal.

The micro pump module 60 drives for the set discharge time, at the prescribed discharge speed set based on the previously described basic data and discharge data.

Herein, on clicking on "Return" on the "Micro pump control" screen shown in FIG. 30, a "Micro pump system" screen shown in FIG. 34 is displayed. The micro pump module name, the operation status, the additional infusion time, and the discharge finishing time are displayed on this screen.

The micro pump module 60 drives for the discharge time, at the discharge speed set based on the previously described basic data and discharge data, and finishes (stops) (ST235). The PC 20 also stops a drive count of the PC 20 itself when the set drive time has elapsed (a drive stop, ST105).

Next, a description will be given of an additional infusion. When driving the fluid conveyance device 50, when carrying out the additional infusion of the fluid, an additional infusion amount is input into an "Additional infusion amount" area on the "Discharge progress graph" screen shown in FIG. 32, in the case of the single drive, and on the "Discharge progress graph" screen shown in FIG. 33, in the case of the multi-drive. A description will be given exemplifying with the case of the single drive.

Figure 35:
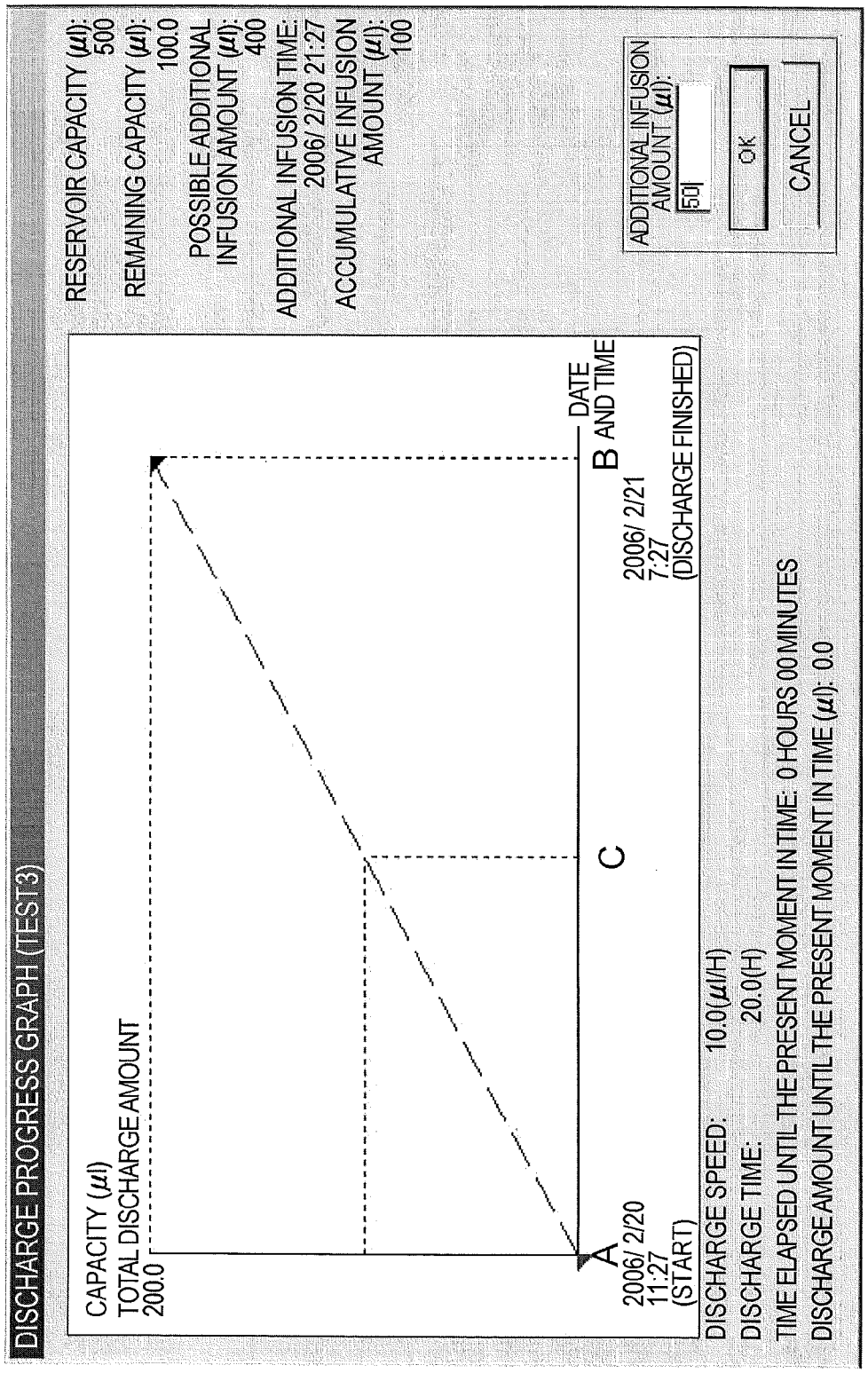
FIG. 35 is a discharge progress graph showing a condition setting an additional infusion amount of the chemical liquid.
Figure 36:
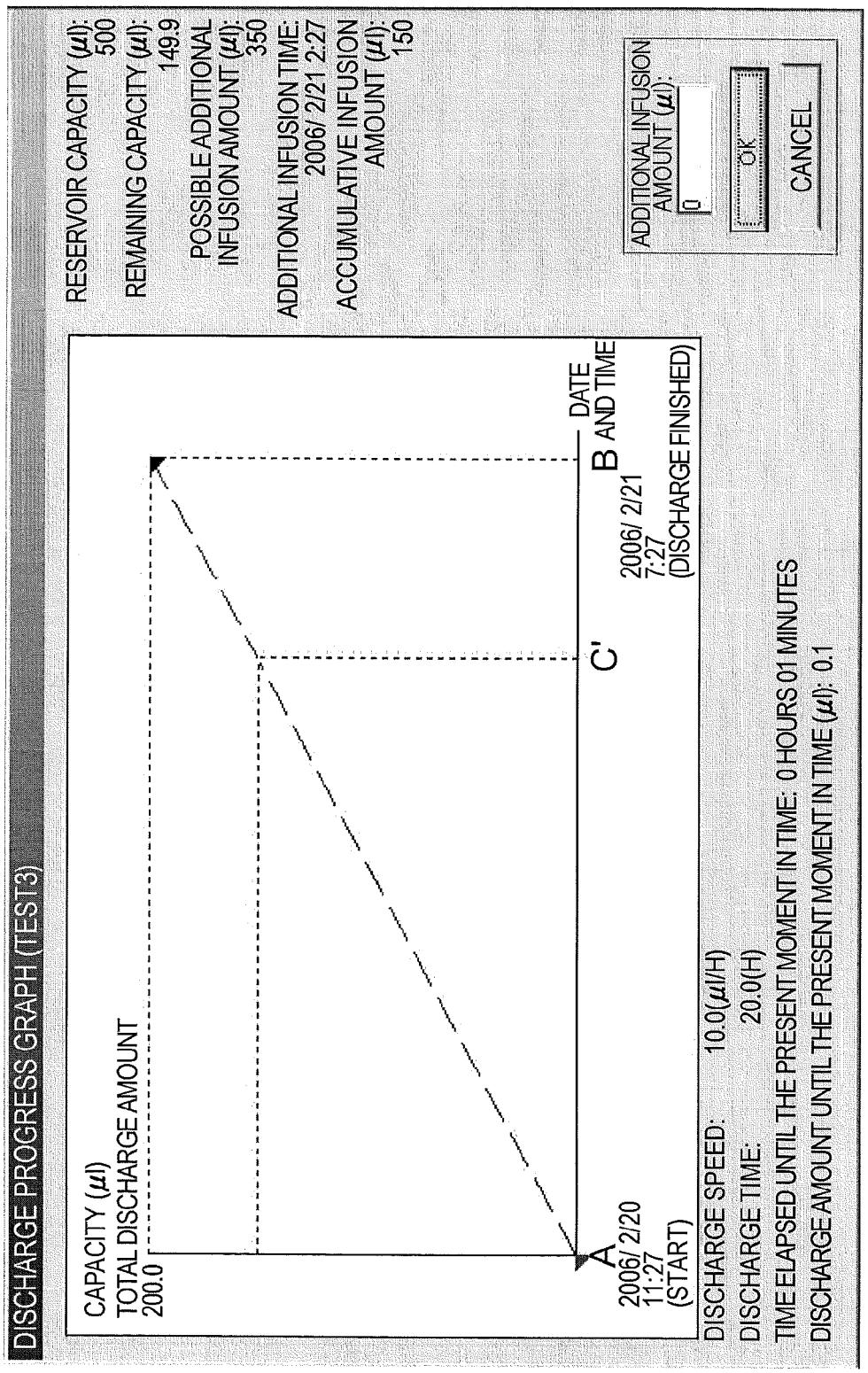
FIG. 36 is a discharge progress graph showing a condition in which the additional infusion amount of the chemical liquid has been set.

On an exemplification screen shown in FIG. 35, an additional infusion amount of 50 µl having been input is shown. Herein, on clicking on "OK", a remaining capacity, a possible additional infusion amount, the additional infusion time, and the accumulative infusion amount are calculated and displayed. Then, a position of reference character C shown in FIG. 35 being an additional infusion scheduled time at an initial stage, a changed additional infusion time is displayed in a position of reference character C' shown in FIG. 36. At this stage, an "Additional infusion amount" area is reset to zero.

In the case of the multi-drive too, it being possible to set the additional infusion amount in the same way as with the single drive, the additional infusion time is displayed in a position indicated by reference character H, as shown in FIG. 33.

As the "Micro pump control" screen shown in FIG. 30 is displayed on the display screen of the display 22, on clicking on "Return" on this screen, a "Micro pump system" screen shown in FIG. 34 is displayed. The pump name, operation status, additional infusion time, and discharge finishing time are displayed on the screen. The operation status is displayed as "Operation in progress".

In the embodiment, when reaching a prescribed time range soon before the additional infusion time or the discharge finishing time, the "Operation in progress" display flashes as an alert. For example, in the event that the prescribed time is set at 24 hours, the alert is displayed when 24 hours are reached. Then, on clicking on "Finish" on the "Micro pump system" screen shown in FIG. 34, the screen is closed.

Continuing, a description will be given of a stopping of the fluid conveyance device 50 after the discharge of the fluid has finished (after the drive has finished), and during the discharge, and of a discharge information data confirmation method. A description will be given exemplifying with a case assuming a confirmation of the micro pump module with the micro pump name "TEST 1".

Figure 37:
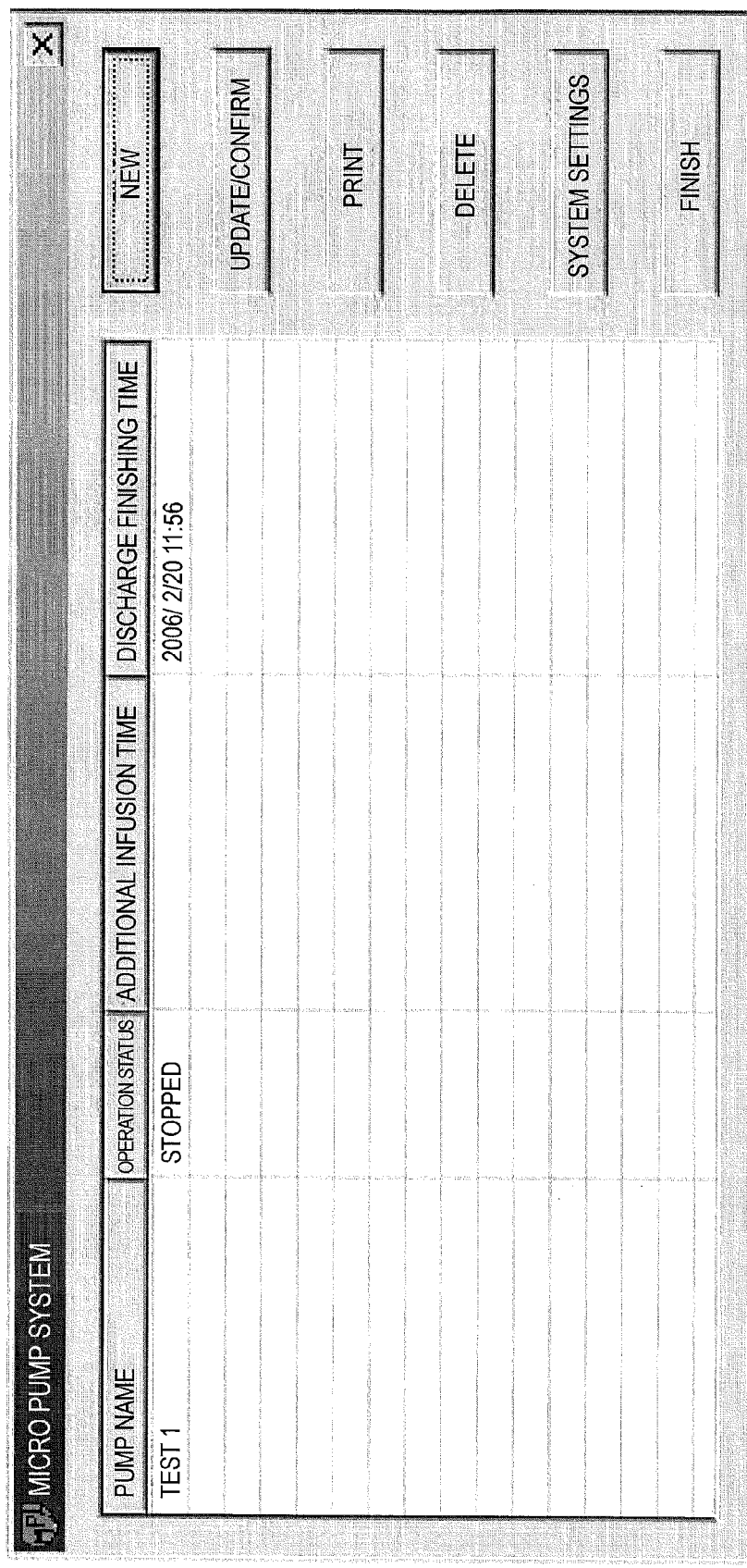
FIG. 37 is an illustration showing a condition in which a discharge of the chemical liquid has finished.

First, a description will be given of a case confirming discharge information from the discharge finishing time onwards. Within a prescribed time (for example, within 12 hours) after the discharge finishing time, the fluid conveyance device 50 is removed from the living organism which is the subject, and mounted on the communication device 30. On selecting "TEST 1" on a "Micro pump system" screen shown in FIG. 37, and clicking on "Update/Confirm", a "Micro pump control" screen shown in FIG. 38, and a "Discharge Progress Graph" screen shown in FIG. 39, are displayed. It is preferable that this graph is distinguished from the discharge plan graph by the color red, or the like.

Figure 38:
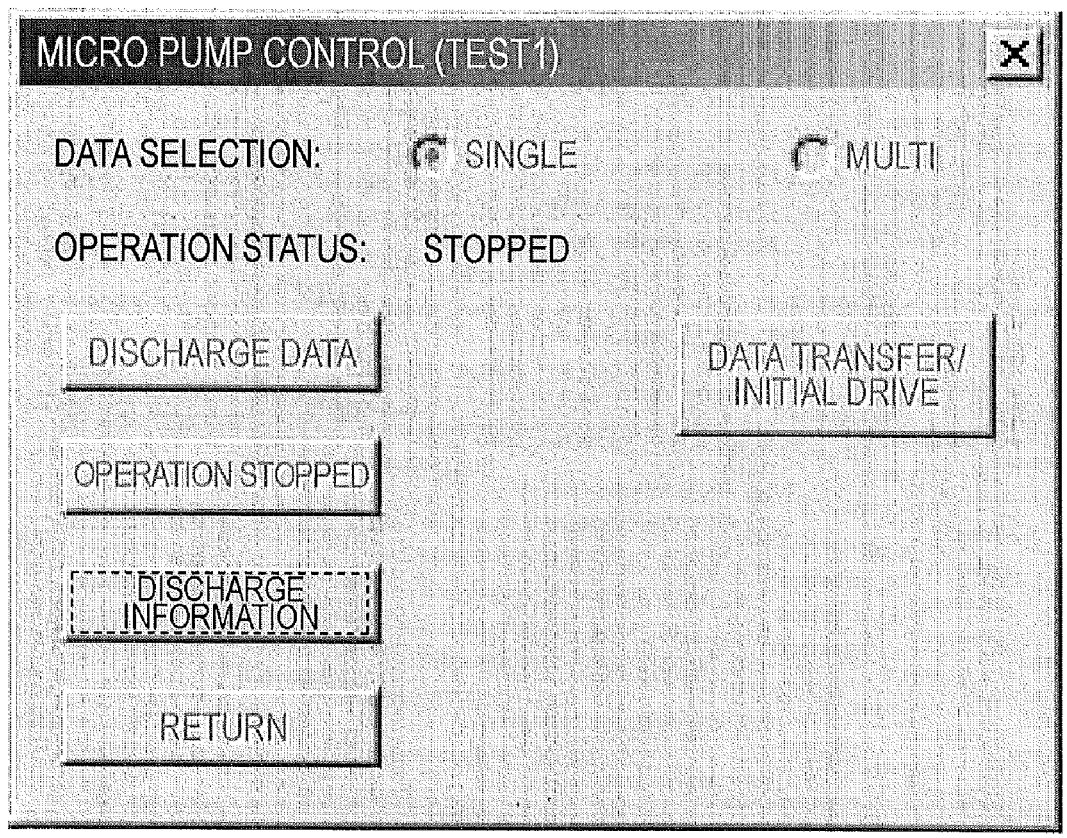
FIG. 38 is an illustration confirming the condition in which the discharge of the chemical liquid has finished.
Figure 39:
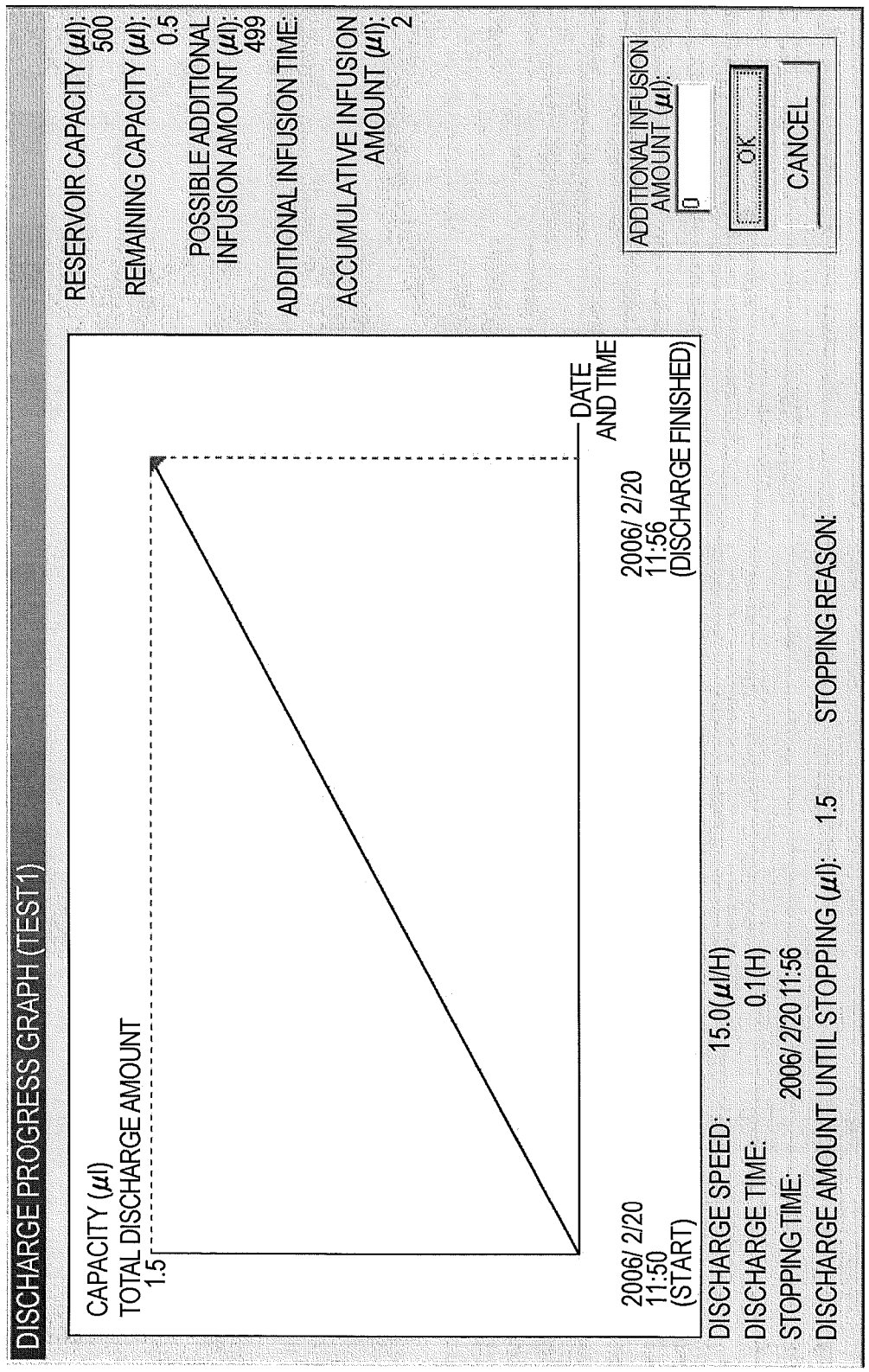
FIG. 39 is a discharge progress graph showing the condition in which the discharge of the chemical liquid has finished.
Figure 40:
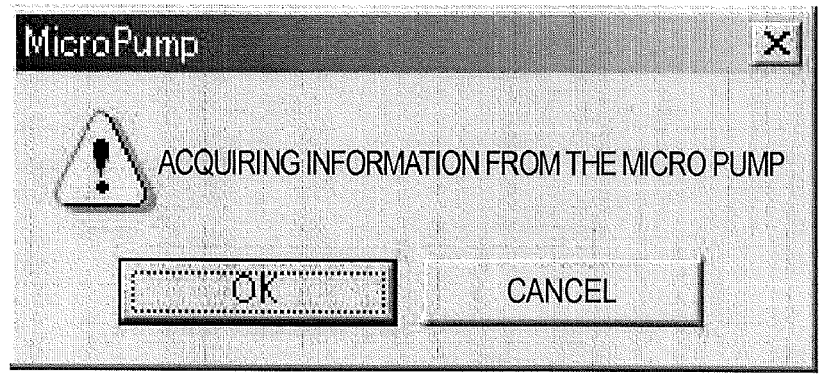
FIG. 40 is an illustration of acquiring discharge information data on the drive of the fluid conveyance device.

The operating status is displayed as "Stopped" on the "Micro pump control" screen of FIG. 38. Also, a graph showing the discharge progress is displayed on the "Discharge Progress Graph" screen. On clicking on "Discharge information" on the "Micro pump control" screen, a screen saying "Acquiring information from the micro pump", shown in FIG. 40, is displayed. On clicking on "OK/" at this point, a "Micro pump discharge information" screen shown in FIG. 41 is displayed.

Figure 41:
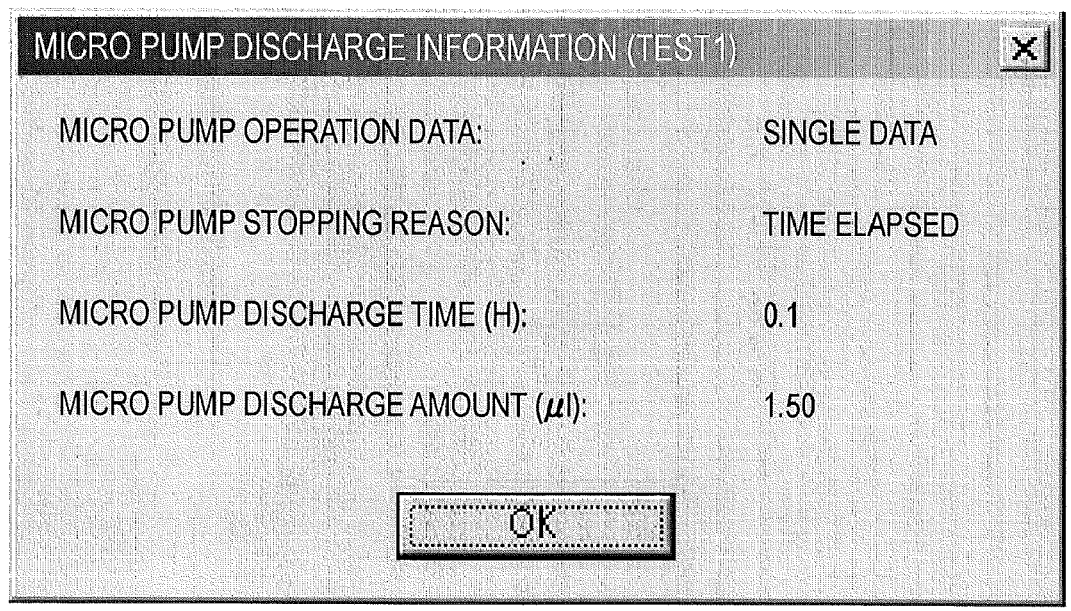
FIG. 41 is an illustration showing a result of the drive of the fluid conveyance device.
Figure 42:
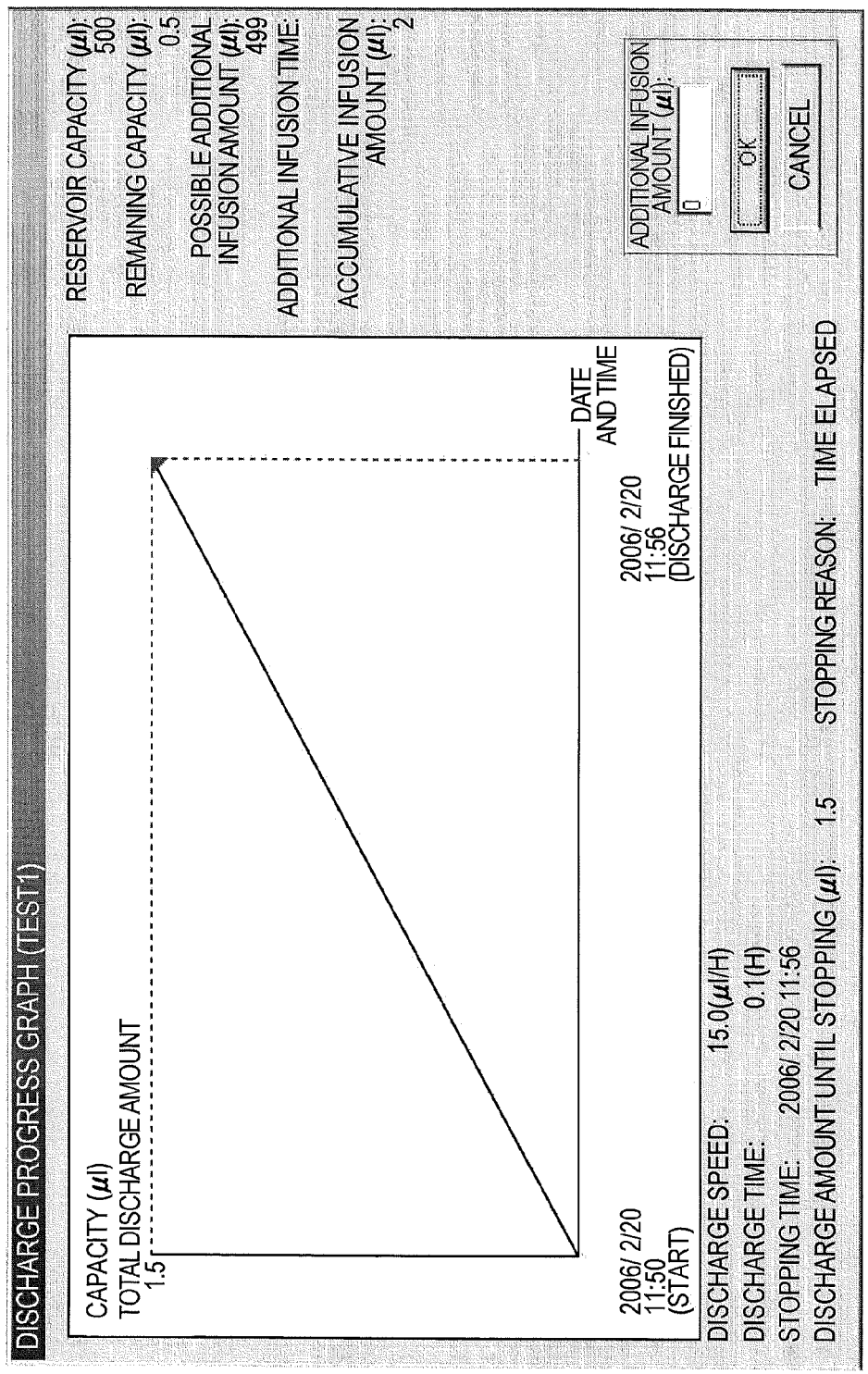
FIG. 42 is a discharge progress graph showing the result of the drive of the fluid conveyance device.
Figure 43:
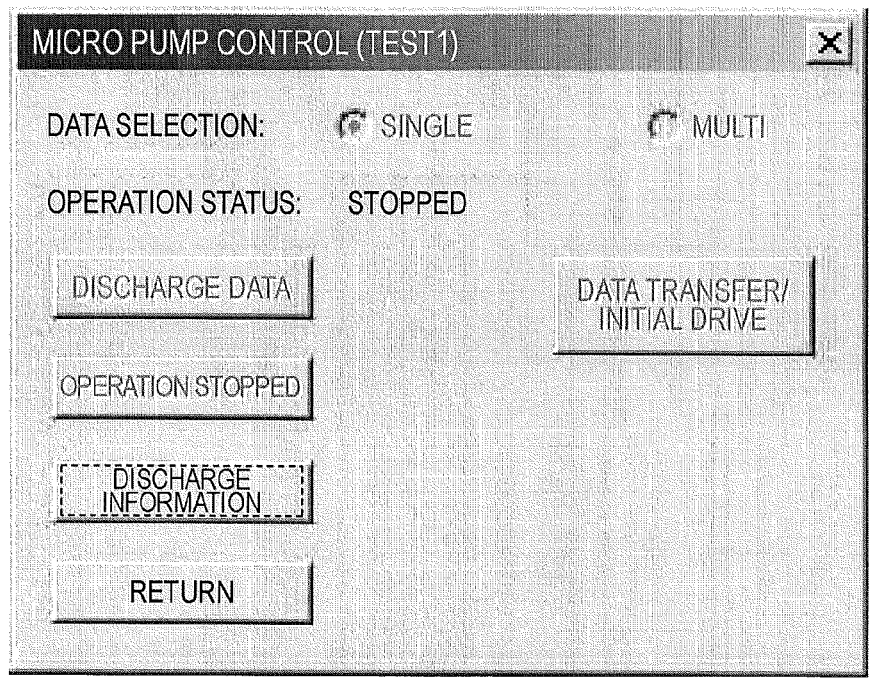
FIG. 43 is an illustration showing that the fluid conveyance device is stopped.

In FIG. 41, "Time elapsed" being displayed as a micro pump stopping reason, this, indicating that there has been no trouble during the drive period, indicates that the scheduled discharge time has finished, and indicates that the discharge time has been 0.1 hours, and the discharge amount 1.5 µl. Also, in a "Discharge progress graph" shown in FIG. 42, a "Stopping reason" is displayed along with the graph. Then, on clicking on "OK", the process returns to a "Micro pump control" screen shown in FIG. 43.

Next, a description will be given of a case of confirming discharge information before the scheduled discharge finishing time. The fluid conveyance device 50 is removed from the living organism which is the subject, and mounted on the communication device 30. An operation status corresponding to the micro pump name "TEST 1", as the identification code which has been used, is displayed on the "Micro pump system" screen shown in FIG. 34. On clicking on "Update/Confirm", a "Micro pump control" screen shown in FIG. 44, and a "Discharge progress graph" screen shown in FIG. 45, are displayed.

At this time, the operation status is displayed as "Operation in progress" on the "Micro pump control/" screen, and a discharge progress until the present moment in time, indicated by reference character C, is displayed on the "Discharge progress graph" screen.

Figure 44:
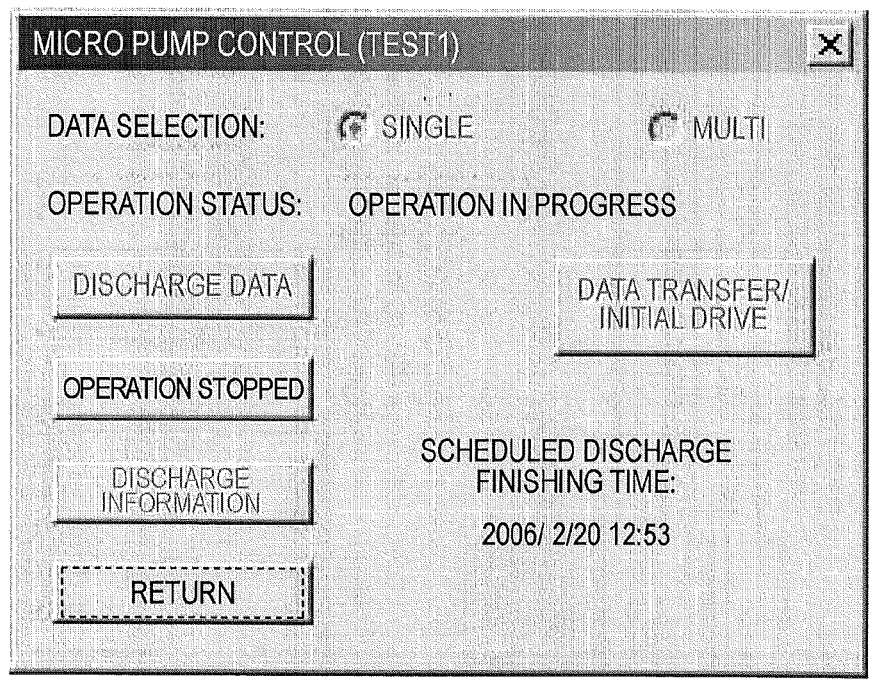
FIG. 44 is an illustration of when inputting an operation stop before a scheduled discharge finishing time.
Figure 45:
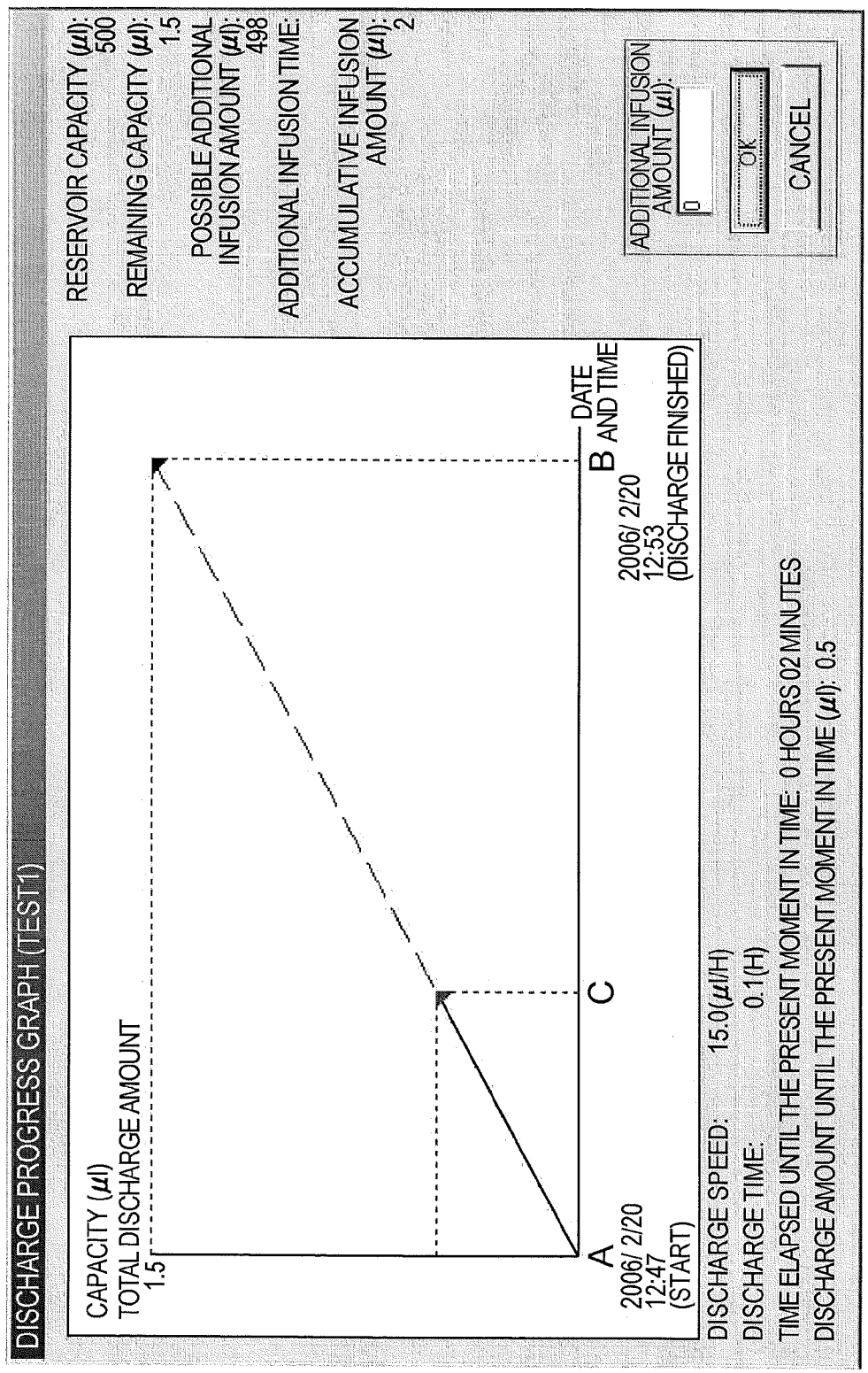
FIG. 45 is a discharge progress graph showing an operation condition at a point of inputting a stopping order before the scheduled discharge finishing time.
Figure 46:
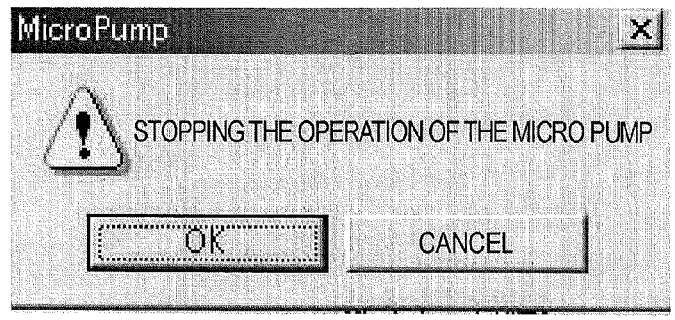
FIG. 46 is an illustration showing the stopping order of the fluid conveyance device.
Figure 47:
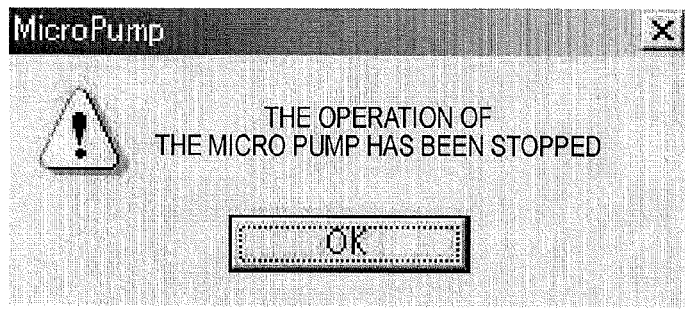
FIG. 47 is an illustration showing a stopping confirmation of the fluid conveyance device.

Herein, by clicking on "Operation stop" on the "Micro pump control" screen shown in FIG. 44, a screen saying "Stopping the micro pump operation", shown in FIG. 46, is displayed. Then, on clicking on "OK", a screen saying "The micro pump operation has been stopped", shown in FIG. 47, is displayed, and the drive of the fluid conveyance device 50 stops.

Figure 48:
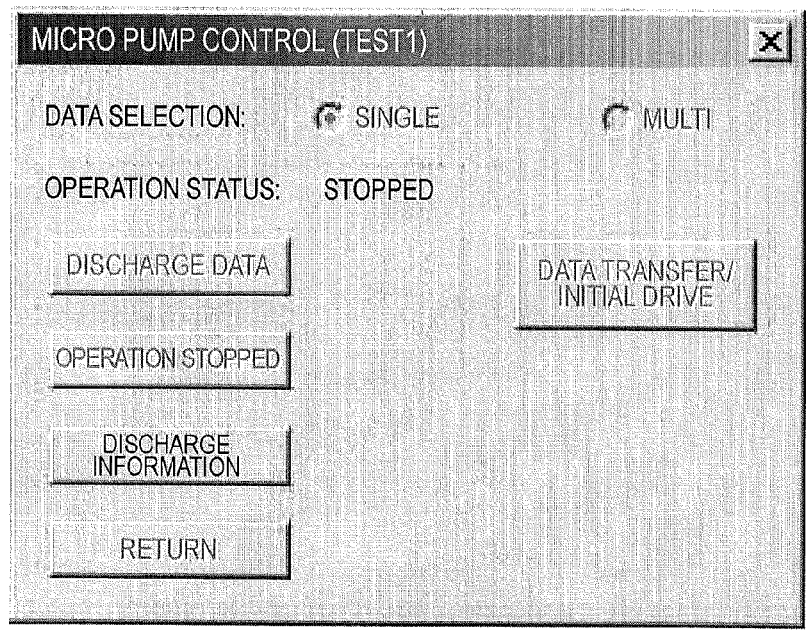
FIG. 48 is an illustration showing a condition in which the fluid conveyance device has stopped.
Figure 49:
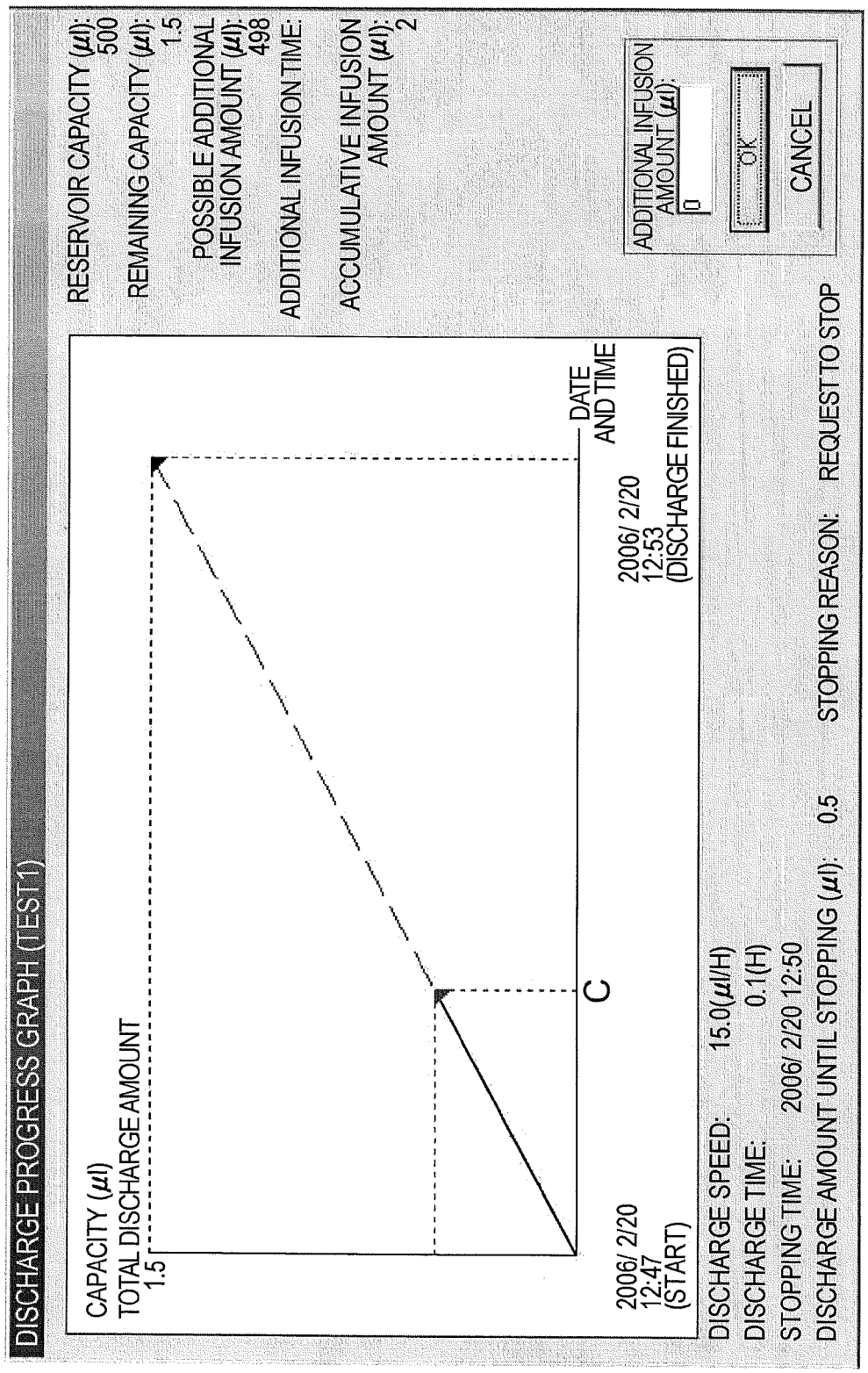
FIG. 49 is a discharge progress graph showing the condition in which the fluid conveyance device has stopped.

Furthermore, on clicking on "OK", a "Micro pump control" screen shown in FIG. 48, and a "Discharge progress graph" shown in FIG. 49, are displayed. The discharge progress graph stops at a position of reference character C, and "Stop requested" is displayed in a stopping reason area. Stop requested means that the user has stopped the fluid conveyance system 10 of t his or her own volition.

Figure 50:
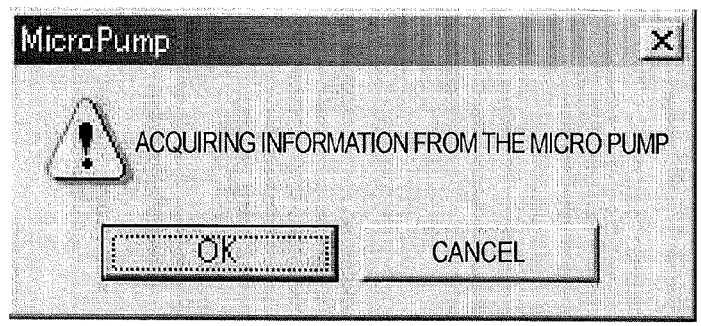
FIG. 50 is an illustration showing an acquisition of discharge information data when the fluid conveyance device has stopped.
Figure 51:
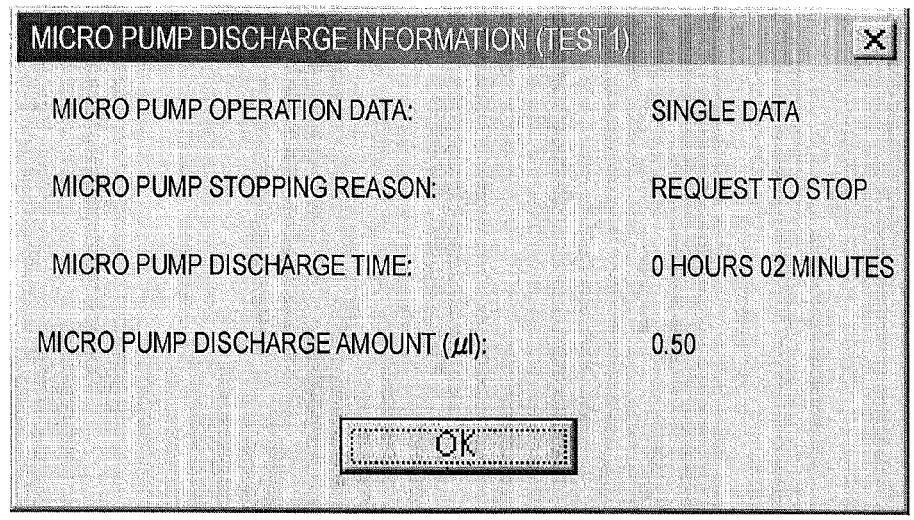
FIG. 51 is an illustration showing the discharge information data when the fluid conveyance device has stopped.

Herein, on clicking on "Discharge information" on the "Micro pump control" screen shown in FIG. 48, a screen saying "Acquiring information from the micro pump", shown in FIG. 50, is displayed. On clicking on "OK" at this point, a "Micro pump discharge information" screen shown in FIG. 51 is displayed. Then, the micro pump stopping reason, the micro pump discharge time, and the micro pump discharge amount are displayed. On clicking on "OK" on this screen, the process returns to the "Micro pump control" screen and the "Discharge progress graph" screen shown in FIG. 48 and FIG. 49.

Figure 52:
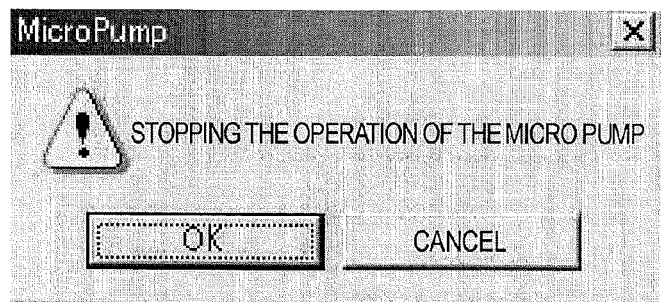
FIG. 52 is an illustration showing a stopping order of the fluid conveyance device due to a voltage reduction of a battery.
Figure 53:
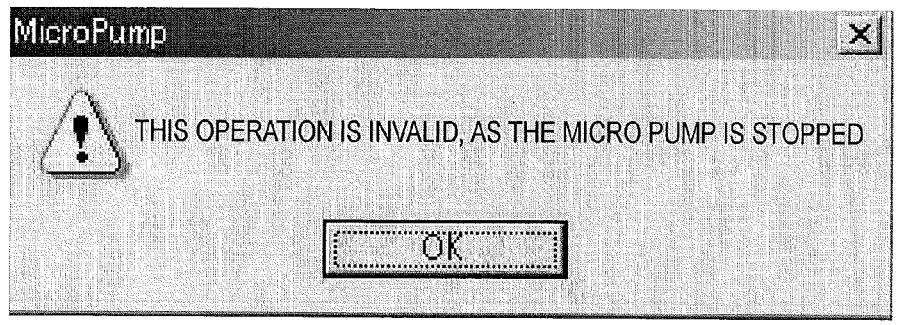
FIG. 53 is an illustration showing a display regarding the stopping order of the fluid conveyance device.
Figure 54:
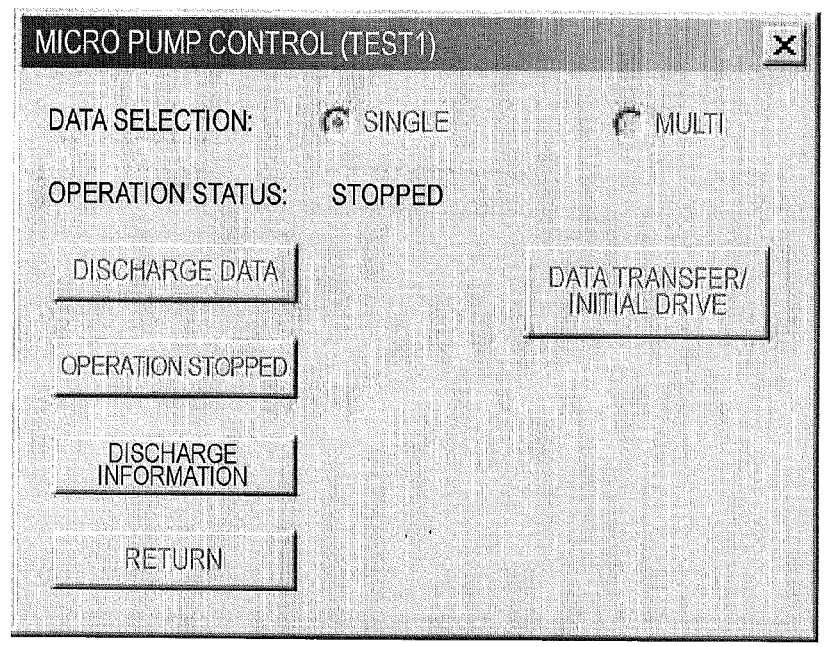
FIG. 54 is an illustration showing a stopped condition of the fluid conveyance device due to the voltage reduction of the battery.

Continuing, a description will be given of a case in which, in a condition in which the fluid conveyance device 50 is being driven (during discharge), a discharge problem has occurred due to a voltage reduction of the battery 45. In this kind of case, the "Micro pump control" screen shown in FIG. 44 is displayed. Herein, on clicking on "Operation stop", a screen saying "Stopping the micro pump operation", shown in FIG. 52, is displayed. On clicking on "OK", a screen saying "This operation is invalid, as the micro pump is stopped", shown in FIG. 53, is displayed. This indicates that the battery voltage has dropped, and that the micro pump module has already stopped. Herein, on clicking on "OK", the process returns to a "Micro pump control/" screen shown in FIG. 54. "Stopped" is displayed in an operation status area.

Figure 55:
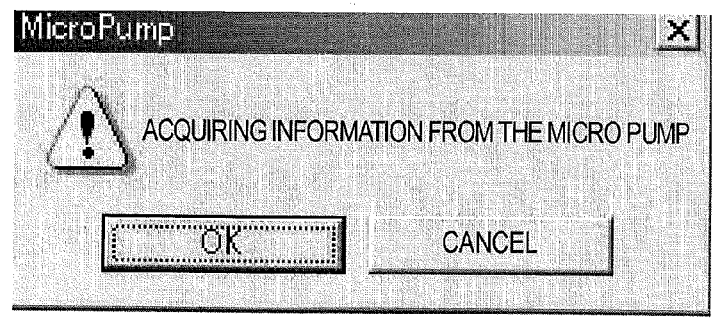
FIG. 55 is an illustration showing a screen acquiring discharge information data when the fluid conveyance device has stopped due to the voltage reduction of the battery.

Then, on clicking on "Discharge information" on the screen, a screen saying "Acquiring information from the micro pump", shown in FIG. 55, is displayed. Herein, on clicking on "OK", a "Micro pump discharge information" screen shown in FIG. 56 is displayed. The micro pump stopping reason, the micro pump drive time, and the micro pump discharge amount are displayed on the screen. The micro pump stopping reason is displayed as "Battery reduction".

As the heretofore described fluid conveyance device 50 drive stop (discharge stop), and discharge information confirmation method, are also the same in the case of the multi-drive, a description will be omitted.

Next, a description will be given of a data correction method after the discharge data registration (shown in FIG. 4B, ST80 or ST180). In the case of the single drive, re-registration is done by clicking on "Discharge data" on the "Micro pump control" screen shown in FIG. 12, and correcting the data to be input on the "Discharge data setting: single" screen shown in FIG. 14.

In the case of the multi-drive, a "Discharge data setting selection: multi" screen shown in FIG. 57 is displayed by clicking on "Discharge data" on the "Micro pump control" screen shown in FIG. 22. Then, the discharge data are corrected by sequentially invalidating setting conditions which are valid from a largest number (No. 5 in FIG. 57).

A description will be given exemplifying with a case of correcting the discharge data of which the setting condition is No. 4. By selecting No. 5, which is valid in FIG. 57, a No. 5 "Discharge data setting: multi", shown in FIG. 58, is displayed. The initially set discharge data of No. 5 is displayed on the screen. Then, on clicking on "Cancel", a "Discharge data setting selection: multi" screen shown in FIG. 59 is displayed. No. 5 is displayed as invalid.

Continuing, No. 4 is selected, a No. 4 "Discharge data setting: multi" screen, shown in FIG. 60, is displayed, and the discharge data are corrected. On clicking on "Register", the process returns to the "Discharge data setting selection: multi" screen shown in FIG. 59. Next, No. 5 is selected, the No. 5 discharge data are re-input on the "Discharge data setting selection: multi" screen, and "Register" is clicked. On doing so, a shift is made to a "Discharge data setting selection: multi" screen shown in FIG. 61, all the setting conditions are displayed as valid, and the correction of the No. 4 discharge data is finished.

Figure 62:
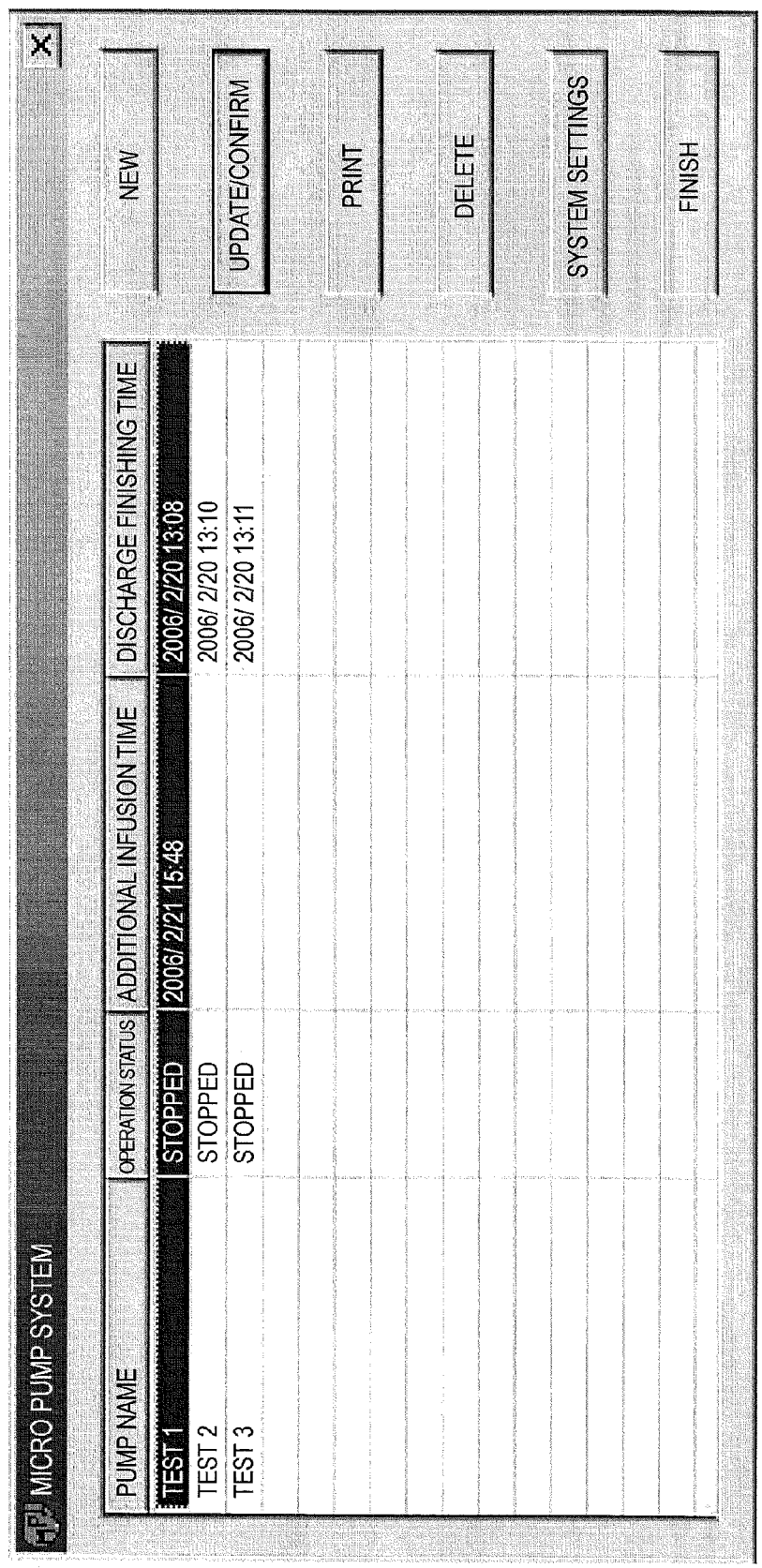
FIG. 62 is an illustration showing a selection operation of the discharge data being input.
Figure 63:
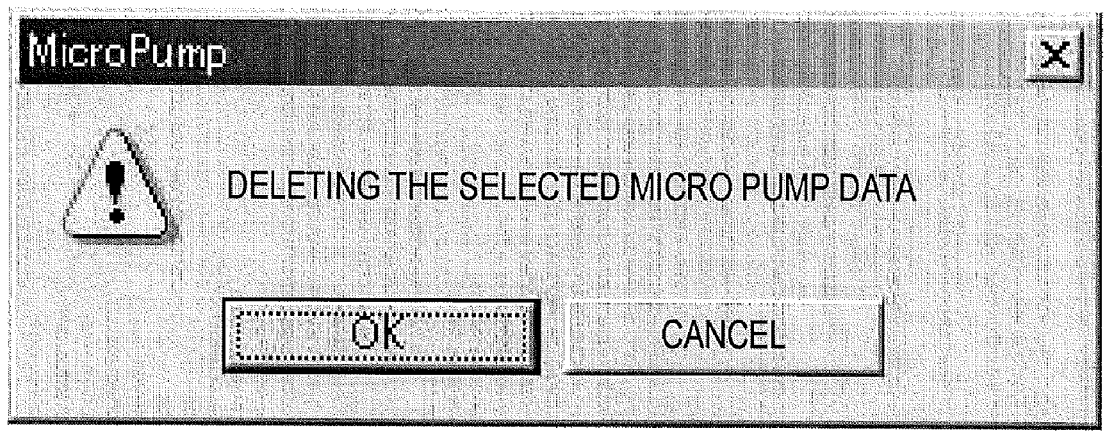
FIG. 63 is an illustration showing a deletion operation of the discharge data being input.
Figure 64:
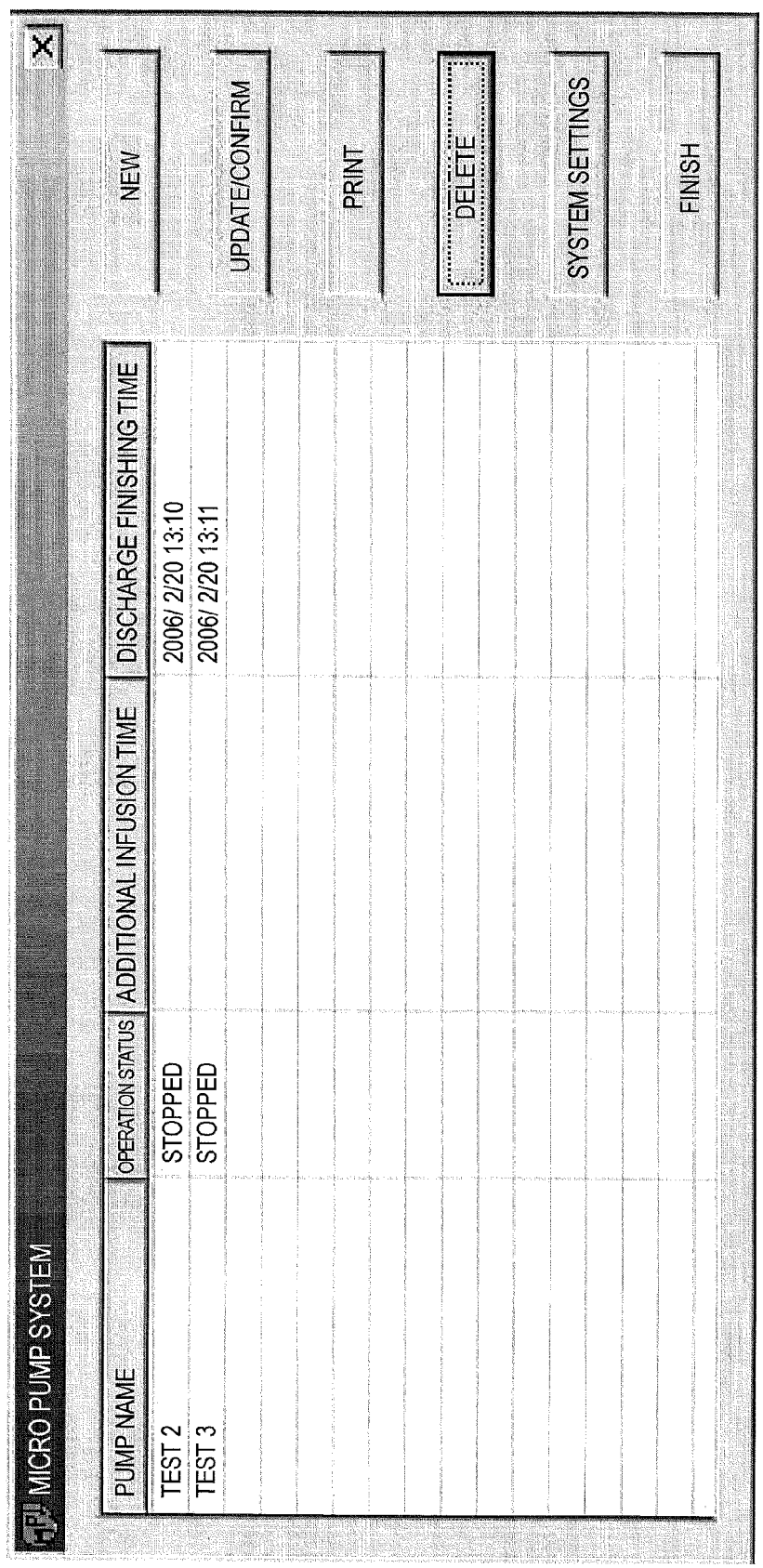
FIG. 64 is an illustration showing a condition in which the discharge data being input have been deleted.

Next, a description will be given of a deletion of the discharge data. A description will be given exemplifying with the multi-drive. First, a. "Micro pump system" screen shown in FIG. 62 is displayed, and a micro pump with a number of a setting condition to be deleted (meaning a drive condition according to multiply-set discharge data) is selected. In FIG. 62, the micro pump called TEST 1 is a subject. Then, on clicking on "Delete", a screen saying "Deleting the data of the selected micro pump", shown in FIG. 63, is displayed, and by clicking on "OK", the micro pump TEST 1 is deleted (shown in FIG. 64).

Figures 65, 66:
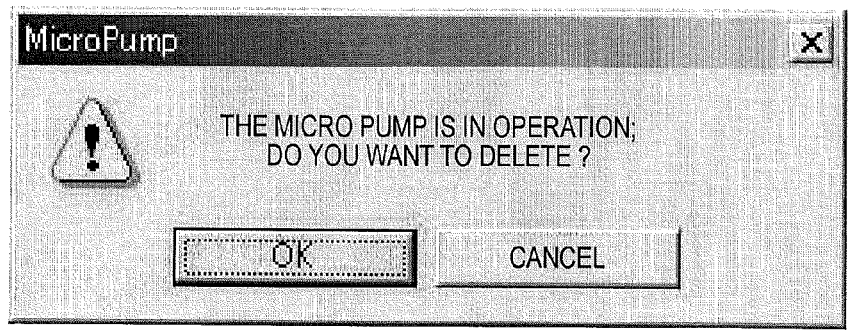
FIG. 65 is an illustration showing a confirmation of the deletion of the discharge data being input.
FIG. 66 is an illustration showing a discharge speed setting and a discharge time setting when reusing.

On attempting to delete a micro pump which is in operation by the heretofore described method, a screen saying "The micro pump is in operation; do you want to delete it?", shown in FIG. 65, is displayed as an alert. Herein, by clicking on "OK", the relevant micro pump name is deleted, even though it is in operation.

Continuing, a description will be given of a case of reusing the fluid conveyance device. Reusing means to newly input the discharge data, and use a fluid conveyance device which has once ceased to be used.

First, after the operation stop (ST105), a micro pump module 60 which has been removed from the communication device 30 is again inserted into the communication device 30. That is, a connection is carried out with the PC 20 as the discharge data processing device. The reservoir 90 is replaced with a new one in a condition in which the tube 62 is inserted (refer to FIG. 3). On doing so, the screen saying "Micro pump name & code input", shown in FIG. 9, is displayed. As the identification data (the micro pump name (ID) and the micro pump code) are already stored in the micro pump module 60, the ID is recognized in the PC 20, via the communication device 30, and displayed on the screen, as shown in FIG. 10.

Herein, on clicking the "OK" button, the "Reservoir initial infusion amount setting (TEST 1)" screen, shown in FIG. 11, is displayed. Then, the initial infusion amount is input. That is, shifting to ST61 shown in FIG. 4B, and continuing through ST65, the discharge data setting is carried out (ST75).

In the PC 20, the micro pump module 60 calculates the battery consumption capacity, calculated from the discharge time and the consumption current until the present moment in time, and the remaining capacity of the battery at the present moment in time from the battery initial capacity.

A "Discharge data settings: single (TEST 1)" screen, shown in FIG. 66, is displayed. A description of a display of this screen will be added. The maximum settable discharge speed is input as the basic data. Values calculated by the PC 20 from the remaining capacity of the battery, and the consumption current and discharge speed of the micro pump module 60, are displayed as the maximum settable discharge time and the maximum settable discharge amount. Also, a set discharge amount is calculated from the discharge speed and the discharge time.

The user carries out the discharge speed setting and the discharge time setting. These being carried out within a range of the remaining capacity of the battery, in the event that a setting which exceeds the range is made, as the screen display flashes and there is an error display, a resetting is done.

After the discharge speed setting and the discharge time setting have been done, on clicking a "Register" button, the discharge data for when reusing are registered. On doing so, the "Micro pump control" screen shown in FIG. 12, and the "Discharge progress plan graph" screen, are displayed. Although a depiction of the "Discharge progress plan graph" is omitted, a relationship between an elapsed drive time and the total discharge amount, calculated from the input discharge data, is displayed.

From ST80 onward, through the same processes as in the case of the previously described initial drive, including also the multi-drive, it is possible to repeatedly reuse until the battery capacity finishes.

Consequently, according to the heretofore described embodiment 1, the individual identification data being input into the memory circuit 53 of the micro pump module 60, as it is possible for the discharge data processing device 20, via the communication device 30, to read and recognize the identification data input into the micro pump module 60, it not being necessary for the user to artificially identify the micro pump module 60 (including also the fluid conveyance device 50), it is possible to prevent a kind of mistake such as inputting erroneous discharge data into the micro pump module 60 to be used, and driving it. This has a benefit of being able to prevent an effect which cannot be ignored when using the fluid conveyance system 10 in medical treatment, a living organism experiment, or the like.

Also, as the discharge data processing device 20, via the communication device 30, reads the individual identification data of the micro pump module 60, it is possible to recognize the micro pump module 60, via the communication device 30, after use too. That is, when driving the fluid conveyance device 50 again after once stopping the drive of the fluid conveyance device 50, as the fluid conveyance device 50 to be reused is recognized by the discharge data processing device 20, it is possible, when reusing too, to prevent a mismatch of the relevant fluid conveyance device data and the relevant fluid conveyance device in the discharge data processing device 20.

Also, by the manufacturer inputting the identification data into the micro pump module 60, and mounting the fluid conveyance device 50 to be driven on the discharge data processing device 20 and the communication device 30, at the time of manufacture, the discharge data processing device 20 being able to recognize the individual data, a bother for the user of inputting the identification data into the discharge data processing device 20 is eliminated.

Also, the identification data includes the identification code of the micro pump module 60, the manufacturing period, and the correction coefficient of the inner diameter of the tube 62. Consequently, as the fluid conveyance device 50 is driven by discharge data in which the fluctuation in the inner diameter of the individual tube 62 to be driven has been corrected by the correction coefficient, it is possible to eliminate an effect of the fluctuation in the inner diameter of the tube 62 on the discharge amount of the fluid.

Also, the identification data can be input from the PC 20, via the communication device 30, into the micro pump module 60. Because of this, in the event that the identification data input in advance into the micro pump module 60 at the time of manufacture should be deleted, it is possible to input the identification data from the PC 20 into the micro pump module 60.

Also, the previously described basic data including the initial battery capacity of the battery 58, and the discharge data including the discharge speed and discharge time of the fluid, it is possible to calculate the remaining capacity of the battery 58 from the consumption current value of the micro pump module 60. By newly setting the discharge speed and discharge time based on the remaining capacity, and driving the fluid conveyance device 50, it is possible to repeatedly reuse the fluid conveyance device until the battery capacity expires.

Furthermore, as it is possible to set the discharge speed and discharge time in accordance with the remaining capacity of the battery, it is possible to prevent the battery capacity expiring and the fluid conveyance device 50 stopping while being used, and to increase safety.

Embodiment 2

Continuing, a description will be given of a fluid conveyance device and a fluid conveyance system according to an embodiment 2. The embodiment has a feature of expressing the identification data by a barcode or a QR code.

Consequently, the description will be mainly of portions differing from the embodiment 1. Although a depiction is omitted, the description will be given referring to FIGS. 1 and 2.

An identification sticker, on which the barcode or QR code is displayed as a display portion expressing the identification data, is stuck in a vicinity of a joint surface (the bottom of the casing 94) of the micro pump module 60 of the embodiment with the communication device 30. Then, a reader which reads the identification data is furnished in a vicinity of a joint surface of the communication device 30 with the micro pump module 60.

On mounting the fluid conveyance device 50 on the communication device 30, the connection terminals 97 and 98 provided on the communication device 30 are connected to the connection terminals 197 and 198 furnished on the micro pump module 60, the reader, recognizing that the fluid conveyance device 50 has been mounted on the communication device 30, reads the identification data displayed on the identification sticker, and inputs the data into the PC 20, the discharge data calculated from the basic data and identification data are input into the micro pump module 60 (refer to FIG. 10) by the same kind of procedure as in the heretofore described flow (refer to FIGS. 4A and 4B), and the driving is done based on the discharge data.

By this means, displaying the identification data by the barcode or the QR code, and recognizing them with the reader, it is possible to prevent the identification data from being deleted by the effect of the static electricity or the like.

Also, by displaying the identification data on the identification sticker by characters, apart from the barcode or the QR code, it is possible for the user to visually perceive the identification data.

In this kind of configuration too, it is preferable to arrange in such a way that, in the event that the reading of the identification data has failed, the identification data can be input from the PC 20 into the micro pump module 60.

The invention not being limited to the heretofore described embodiments, modifications, improvements and the like, within a range which can achieve the object of the invention, are included in the invention.

For example, although, in the heretofore described embodiments, the description is given exemplifying with the fluid conveyance system for injecting the chemical liquid, the fluid conveyance system, not being limited to the chemical liquid, can also be used for conveying a fluid such as water or a saline solution, oil, an aromatic liquid, ink or a gas.

Also, although, in the heretofore described embodiments, the PC 20 is employed as the discharge data processing device, not being limited to the PC, it is possible to make it a system equipped with a discharge data processing device, dedicated to the system, which includes a display and an operating portion.

The setting of the basic data and the discharge data, and the discharge amount setting method, in the fluid conveyance system according to the heretofore described embodiments, being one example, an order thereof, a range of settings done by the manufacturer, and a range of settings done by the user, can be changed in accordance with a utilization of the fluid conveyance system.

Furthermore, although the fluid conveyance system of the embodiment employs a peristaltic type micro pump module, it is possible to employ a different type of miniature pump which can discharge a minute amount. In this kind of case, it is preferable to set the parameters of the basic data and discharge data in accordance with the pump employed.

Also, in the case in which the communication unit is the wired communication, at this point the fluid conveyance device 50 is mounted in a prescribed mounting place. The same applies in the case of employing the infrared ray communication unit.

Also, in the case of the wireless communication unit, after mounting the fluid conveyance device 50 in the prescribed position, it is acceptable to transfer the order to start injecting the chemical.

Consequently, according to the heretofore described embodiments, as a plurality of fluid conveyance devices can be individually identified and selectively used, there is no likelihood of mistaking the fluid conveyance device to be driven when reusing, and, recognizing the remaining capacity of the individual battery, as long as the battery capacity remains, it is possible to repeatedly reuse the fluid conveyance device.

The entire disclosure of Japanese Patent Application Nos: 2006-209518, filed Aug. 1, 2006, 2007-165919, filed Jun. 25, 2007 are expressly incorporated by reference herein.

What is claimed is:

1. A fluid conveyance system comprising:
 a fluid conveyance device including a micro pump module which compresses a flexible tube communicating with a fluid containing receptacle and discharges a fluid, the micro pump module including a RAM memory device that stores individual identification data of the micro pump module and a power source;
 a discharge data processing device which stores basic data for driving the fluid conveyance device; and
 a communication device having a communication unit which interconnects the fluid conveyance device and the discharge data processing device,
 wherein the discharge data processing device inputs discharge data, for discharging a desired discharge amount of a fluid, calculated from the identification data and the basic data read via the communication device, into the RAM memory device via the communication device,
 the fluid conveyance device is driven based on the discharge data, and
 the micro pump module includes a roller base that rotates about an axis of rotation and drives a plurality of pressing shafts perpendicularly oriented to the axis of rotation for compressing the flexible tube,
 the identification data includes at least an identification code of the micro pump module, a manufacturing period, and a correction coefficient for correcting a discharge amount fluctuation due to a fluctuation in inner diameter of the flexible tube, the correction coefficient being represented by a ratio between an inner diameter of a standard tube and an inner diameter of the flexible tube, or by a ratio between a discharge amount of the fluid conveyance device provided with the standard tube and a discharge amount of the fluid conveyance device provided with the flexible tube, and the correction coefficient being used to correct a discharge amount fluctuation resulting from the flexible tube having a different diameter than the standard tube,
 wherein the standard tube has a diameter D and the flexible tube has a diameter d, the correction coefficient being expressed by $R=(d/D)^2 \times 1000$, and $R=1000$ when $D=d$.

2. The fluid conveyance system according to claim 1, wherein
 the power source is a battery,
 the basic data further include an initial battery capacity of the power source,
 the discharge data include a discharge speed and a discharge elapsed time of the fluid,
 the discharge data processing device, including a calculation device which calculates a remaining capacity of the battery from a consumption current value and a discharge time of the micro pump module, transmits a discharge speed and a discharge time of a re-drivable range, based on the remaining capacity, to the RAM memory device, and
 the fluid conveyance device is re-driven based on the discharge speed and the discharge time.

3. The fluid conveyance system according to claim 1, wherein the identification data include at least an identification code, a manufacturing period, and the correction coefficient, and the identification data are input from the discharge data processing device, via the communication device, into the micro pump module.

4. The fluid conveyance system according to claim 1, wherein the identification data include at least an identification code, a manufacturing period, and a correction coefficient, a display portion which displays the identification data is disposed in a position opposite a reader furnished on the communication device of the micro pump module, and the identification data is input by the reader, via the communication device, from the display portion into the discharge data processing device, and discharge data calculated based on the basic data and the identification data are transmitted to the micro pump module via the communication device.

5. A fluid conveyance device comprising:

a micro pump module which compresses a flexible tube communicating with a fluid containing receptacle and discharges a fluid, the micro pump module including a RAM memory device that stores individual identification data of the micro pump module and a power source, wherein a discharge data processing device, which stores basic data for driving the fluid conveyance device, inputs discharge data for discharging a desired discharge amount of a fluid, calculated from the identification data and the basic data read via a communication device, which has a communication unit which interconnects the fluid conveyance device and the discharge data processing device, into the RAM memory device via the communication device, the fluid conveyance device is driven based on the discharge data, the micro pump module includes a roller base that rotates about an axis of rotation and drives a plurality of pressing shafts perpendicularly oriented to the axis of rotation for compressing the flexible tube, and the identification data includes at least an identification code of the micro pump module, a manufacturing period, and a correction coefficient for correcting a discharge amount fluctuation due to a fluctuation in inner diameter of the flexible tube, the correction coefficient being represented by a ratio between an inner diameter of a standard tube and an inner diameter of the flexible tube, or by a ratio between a discharge amount of the fluid conveyance device provided with the standard tube and a discharge amount of the fluid conveyance device provided with the flexible tube, and the correction coefficient being used to correct a discharge amount fluctuation resulting from the flexible tube having a different diameter than the standard tube, wherein the standard tube has a diameter D and the flexible tube has a diameter d, the correction coefficient being expressed by $R=(d/D)^2 \times 1000$, and $R=1000$ when $D=d$.

6. The fluid conveyance system of claim 1, wherein the RAM memory device updates and stores identification data as information changes over time.

7. The fluid conveyance device of claim 5, wherein the RAM memory device updates and stores identification data as information changes over time.

* * * * *